United States Patent [19]

Ryser et al.

[11] Patent Number: 4,701,521

[45] Date of Patent: Oct. 20, 1987

[54] METHOD OF EFFECTING CELLULAR UPTAKE OF MOLECULES

[75] Inventors: Hugues J. Ryser, Concord; Wei-Chiang Shen, Needham, both of Mass.

[73] Assignee: The Trustees of Boston University, Boston, Mass.

[21] Appl. No.: 2,368

[22] Filed: Jan. 10, 1979

Related U.S. Application Data

[63] Continuation-in-part of Ser. No. 925,075, Jul. 17, 1978, abandoned, which is a continuation-in-part of Ser. No. 869,894, Jan. 16, 1978, abandoned.

[51] Int. Cl.$^4$ ............................................. C07K 9/00
[52] U.S. Cl. .................................................. 530/322
[58] Field of Search .................... 424/78; 260/112.5 R; 530/322

[56] References Cited

U.S. PATENT DOCUMENTS

| | | | |
|---|---|---|---|
| 3,946,035 | 3/1976 | Jacquet et al. | 424/78 |
| 4,024,222 | 5/1977 | Ts'o et al. | 260/112.5 R |
| 4,024,241 | 5/1977 | Levy | 260/112.5 R |
| 4,046,722 | 9/1977 | Rowland | 424/85 |
| 4,055,635 | 10/1977 | Green et al. | 424/78 |
| 4,088,639 | 5/1978 | Zappelli et al. | 260/112.5 R |
| 4,129,560 | 12/1978 | Zoltobrocki | 260/112.5 R |
| 4,182,654 | 1/1980 | Royer | 260/112.5 R |
| 4,315,074 | 2/1982 | Royer | 260/112.5 R |
| 4,336,185 | 6/1982 | Niswender | 260/112.5 R |
| 4,336,188 | 6/1982 | Zappelli et al. | 260/112.5 R |
| 4,376,765 | 3/1983 | Trouet et al. | 260/112.5 R |
| 4,386,026 | 5/1983 | Ponpipom et al. | 260/112.5 R |
| 4,389,395 | 6/1983 | Lerner et al. | 260/112.5 R |

FOREIGN PATENT DOCUMENTS 1446536  8/1976  United Kingdom .

OTHER PUBLICATIONS

Torchilin–Chem. Abst., vol. 84 (1976), p. 40, 256d.
Lacey, Jr. et al., J. Pharm. Sci., 64 (1975), 473–477.
Wagner et al., Biochemistry, 7 (1968), 1771–1777.
Yu et al., Biochemistry, 13 (1974), 3713–3717.
Carroll, Biochemistry, 11 (1972), 426–432.
Chem. Abstr., vol. 95 (1981), 98290d.
Chem. Abstr., vol. 96 (1982), 200135s.
Chem. Abstr., vol. 98 (1983), 143824f.
Chem. Abstr., vol. 98 (1983), 157399h.
Chem. Abstr., vol. 73 (1970), 52230b.
Chem. Abstr., vol. 73 (1970), 94528k.
Chem. Abstr., vol. 69 (1968), 8392z.
Chem. Abstr., vol. 94 (1981), 192661b.
Chem. Abstr., vol. 90 (1979), 138190b.
Chem. Abstr., vol. 91 (1979), 175709.
Chem. Abstr., vol. 93 (1980), 163200n.
Chem. Abstr., vol. 84 (1976), 129088y.
Chem. Abstr., vol. 82 (1975), 86584w.
Chem. Abstr., vol. 80 (1974), 133803n.
Chem. Abstr., vol. 84 (1976), 132299y.
Chem. Abstr., vol. 68 (1968), 9320r.
Chem. Abstr., vol. 74 (1971), 71722a.
Chem. Abstr., vol. 83 (1975), 79591p.
Chem. Abstr., vol. 82 (1975), 43708x.
Chem. Abstr., vol. 88 (1978), 191385d.
Chem. Abstr., vol. 85 (1976), 21822q.
Chem. Abstr., vol. 80 (1974), 108480x.
Chem. Abstr., vol. 77 (1972), 19939z.
Chem. Abstr., vol. 82 (1975), 125595x.
Ryser, "Poly(Amino Acids) As Enhancers in the Cellular Uptake of Macromolecules", in Peptides, Polypeptides & Proteins, Blout et al., Editors, John Wiley & Sons, Inc., New York, pp. 617 to 628 (1974).

*Primary Examiner*—Delbert R. Phillips
*Attorney, Agent, or Firm*—Hamilton, Brook, Smith & Reynolds

[57] ABSTRACT

A method of effecting cellular uptake of molecules which are either excluded from cells or poorly transported into cells is disclosed wherein such molecules are covalently bonded to a cationic polymer which serves as a transport carrier to transport the molecules into cells.

1 Claim, 12 Drawing Figures

METHOD OF EFFECTING CELLULAR UPTAKE OF MOLECULES

GOVERNMENT SPONSORSHIP

Work relating to this invention was partially supported by Grant No. 5 RO1 CA14551 from the National Institutes of Health.

RELATED APPLICATIONS

This is a continuation-in-part of Ser. No. 925,075, filed July 17, 1978, now abandoned, which in turn was a continuation-in-part of Ser. No. 869,894, filed Jan. 16, 1978, now abandoned.

BACKGROUND OF THE INVENTION

1. Field of the Invention

This invention is in the fields of cell biology and cellular and molecular pharmacology.

2. Description of the Prior Art

It is known that many molecules of a wide variety are not transported, or are poorly transported, into living cells. Macromolecules, for example, such as proteins, nucleic acids, and polysaccharides, are not suited for diffusion or active transport through cell membranes simply because of their size. In order to allow such macromolecules to pass into cells, cell membranes form small vesicles which migrate from the periphery to the interior of the cell, a process known as pinocytosis. This form of transport is generally less efficient, however, than the diffusion or active transport of smaller molecules, and thus, the cellular uptake of macromolecules is limited.

The most common reason why many small molecules are excluded or poorly transported into cells is their ionic charge. The mere presence of either negatively or positively charged groups severely limits cellular uptake of small molecules, such as nucleotides, nucleotide analogues, cofactors and a number of drugs.

While the two reasons discussed above are the main factors which limit cellular uptake of molecules, there are undoubtedly other reasons as well. Because of these limitations in the cellular uptake of certain molecules, there has been a large amount of research directed to overcoming or obviating inadequate cellular transport of such molecules.

One method previously suggested by Ryser involves the use of cationic polymers, i.e., macromolecules which bear a sequence of positive charges. In this method, it was found that cellular uptake of some molecules could be improved by the simple presence in the experimental medium of such cationic polymers, especially homopolymers of positively charged amino acids such as poly-L-lysines, poly-D-lysines and poly-L-ornithines. See Ryser, H. J.-P., "Uptake of Protein by Mammalian Cells: An Underdeveloped Area", *Science*, 159, 390–6 (1968); and Ryser, H. J.-P., "Transport of Macromolecules, Especially Proteins Into Mammalian Cells, Proc. Fourth Internat. Congress on Pharmacology (1970); and, Ryser, H. J.-P., "Poly(amino acids) as enhancers in the cellular uptake of macromolecules, in 'Peptides, Polypeptides and Proteins'", Proceedings of the Rehovot Symposium on Polyamino Acids, Polypeptides and Proteins and their Biological Implications, May 1974, E. R. Blout, F. A. Bovey, M. Goodman and N. Lotan, Eds, John Wiley and Sons, Inc., New York, pp 617–628 (1974). It has also been shown that protoplasts prepared from mesophyll of *Nicotiana tabacum* can be infected by adding purified tobacco mosaic virus particles to a protoplast suspension in the presence of poly-L-ornithine whereas infection does not occur if poly-L-ornithine is not present. See Takebe, I. and Otsuki, Y., "Infection of Tobacco Mesophyll Protoplasts by Tobacco Mosaic Virus," *Proc. N.A.S.*, 64, pp 843–8 (1969). The presence of strongly positively charged proteins, such as histones, also increased cellular uptake of albumin. See Ryser, H. J.-P. and Hancock, R., *Science*, 150, pp 501–3 (1965).

While this prior technique did improve cellular uptake of some macromolecules, it suffered from a number of deficiencies. For example, only minimal enhancement was found for some proteins, e.g., horseradish peroxidase. Also, the cationic polymers form, at most, reversible complexes with the molecule to be transported and may interact at random with other molecules in the medium which means that the enhancement lacks specificity and reproducibility. Further, it was found that enhancement required using cationic polymers of relatively high molecular weight, and that, for example, cationic polymers with molecular weights around 6000 were practically ineffective. See Ryser, H. J.-P., "A Membrane Effect of Basic Polymers Dependent on Molecular Size", *Nature, Lond.*, 215, pp 934–6 (1967). In summary, this technique provided some enhancement of cellular uptake for some macromolecules, but even in these cases enhancement was only modest, non-selective, variable and required polymers of large molecular size.

Other researchers have covalently linked enzymes to polymers for purposes other than cellular transport. Goldstein et al., in U.S. Pat. No. 4,013,511, for example, describe a method for insolubilizing or immobilizing enzymes by covalently bonding the enzymes to anionic or cationic resins. In this method, polymeric resins are formed by reacting ethylene-maleic anhydride copolymer (EMA) and a suitable diamine, such as hydrazine, p,p'-diaminophenyl methane or a primary aliphatic diamine such as 2,6-diaminohexane. Such resins are anionic, but can be made cationic by reacting them with N,N-dimethyl-1,3-propanediamine (DMPA) in the presence of an activating agent, such as dicylohexylcarbodiimide (DCC). Both the anionic and cationic polymeric resins can be covalently coupled to biologically active proteins such as enzymes.

Goldstein et al. ('511) point out that immobilized enzyme derivatives serve as specific easily removable catalysts that can be used repeatedly in columns and in batch reactors. The invention described in U.S. Pat. No. 4,013,511 appears to be a continuation of earlier work by the same researchers which are generally directed to insolubilizing enzymes by reacting them with polymers. See, for example, U.S. Pat. Nos. 3,627,640; 3,650,900; 3,650,901; and 3,706,633. All of these patents contain a description of various techniques which can be used to bond enzymes to polymers. Another patent, namely U.S. Pat. No. 3,374,112, issued to Katchalski et al., discloses the covalent bonding of enzymes to a water insoluble copolymer of L-leucine and p-aminophenyl-DL-alanine, for a similar purpose.

It has also been reported that cationized ferritin can be formed by carbodiimide coupling of horse spleen ferritin to a diamine, namely, N,N-dimethyl-1,3-propanediamine. Cationized ferritin was proposed by these researchers as a tracer molecule for the detection of negatively charged groups on the surface of red blood cells. See Danon, D., Goldstein, L., Marikovsky, Y. and Skutelsky, E., "Use of Cationized Ferritin as a Label of Negative Charges on Cell Surfaces," *J. Ultrastructure Res.*, 38, pp 500–512 (1972); and Grinnell, F., Tobleman, M. Q., and Hackenbrock, C. R., "The Distribution and Mobility of Anionic Sites on the Surfaces of Baby Hamster Kidney Cells," *J. Cell Biol.*, 66, 470 (1975).

A low density lipoprotein was cationized using the Danon et al. technique and shown to accumulate in human fibroblasts. Since low density lipoprotein carries cholesterol into the cells, it was noted that the cationized form of the low density lipoprotein provided an model system for the study of the pathologic consequences at the cellular level of massive deposition of cholesteryl ester. See Basu, S. K., Anderson, G. W., Goldstein, J. L., and Brown, M. S., "Metabolism of Cationized Lipoproteins by Human Fibroblasts", *J. Cell Biology*, 74, pp 119–135 (1977). This method of cationizing a protein has several weaknesses as a method to enhance cellular uptake. For example, the diamine used is not digested by intracellular proteolytic enzymes and thus may accumulate in cells and cause cytotoxic effects. Further, adequate cationization requires attachment of a large number of diamine molecules to carboxyl groups of proteins. Thus, it has been reported that 70% of all of the carboxyl groups of LDL have been modified by this procedure. Such drastic modification would be expected to destroy the biological activity of most functional proteins. Additionally, the diamine used is not suitable as a carrier to enhance the cell penetration of small molecules.

Recent work has been directed to covalently bonding drugs, including anti-cancer drugs, to immunoglobulins or immunoglobulin derivatives for the purpose of directing drugs to cells bearing specific antigens. U.S. Pat. No. 4,046,722, for example, describes an immunoglobulin specific for antigens on the surface of cells to be killed, to which 1–10 polymer carrier molecules are covalently bonded, the polymer carriers having themselves about 5–500 molecules of a cytotoxic drug covalently bonded to them. These polymer carriers have molecular weights of 5000–500,000 and free carboxyl, amino or cycloimidocarbonate groups so that cytotoxic drugs containing amino or carboxyl groups can be covalently bonded thereto. Poly(amino acids), including polylysine, polyaspartic acid, polyarginine, etc., are described as potentially useful polymer carriers for this purpose.

Similar attempts to increase drug selectivity by attaching the drug to antibodies are described in British Patent Specification 1,446,536 and South African patent application 76-2966. These patents disclose techniques for covalently bonding anti-cancer drugs to antibodies or antigen-binding fragments of antibodies specific for tumor antigens.

Still further work involving covalently bonding a potential anti-cancer drug to a polymeric carrier is described in AACR Abstract 454, *Proceedings of AACR and ASCO*, p 114 (1978). In this work, 6-aminonicotinamide was covalently linked to poly-L-lysine to lower the central nervous toxicity of this drug.

SUMMARY OF THE INVENTION

This invention relates to a method for effecting or enhancing cellular uptake of molecules which are either excluded from or are taken up poorly by cells. The method is based upon the discovery that cellular uptake of such molecules can be increased if a conjugate of these molecules is formed by covalently bonding them to a cationic polymer. For reasons not entirely understood, the cationic polymer appears to serve as a transport carrier for the excluded molecule, and the conjugated molecule is transported through cell membranes in a much more effective manner than the unconjugated molecule. Thus, the method of enhancing the cellular uptake of molecules comprises first covalently bonding them to a cationic polymer and subsequently administering the resulting conjugate to cells.

This method can be used to enhance cellular uptake of macromolecules which normally are not effectively transported into cells. These macromolecules include proteins, such as enzymes, growth factors or other regulatory proteins, peptides, polypeptide hormones, lectins, antigens, antibodies or fragments thereof; informational macromolecules such as DNA and RNA; subcellular organelles and supermolecular particles such as chromosomes or components thereof; polysaccharides; etc. Importantly, the method also has application to cellular uptake of excluded small molecules including nucleotides, nucleotide analogues, cofactors (e.g., cyanocobalamin), and drugs in general. As used herein, the term "drug" is used in a broad sense to mean any substance used to treat a disease or to modify a condition in living organisms, particularly including human beings and other mammals.

The degree of enhancement of cellular uptake has been found to be surprising and dramatic. For some proteins, for example, the formation of a conjugate according to this invention has been found to increase cellular uptake by factors ranging up to several hundred-fold.

In addition to the dramatic enhancement of cellular uptake, this method has other significant advantages. For example, this method may require the modification of only one carboxyl group located on the surface of a functional protein. Such minor modification is not likely to destroy biological function. Thus, for example, a biologically active enzyme can be conjugated and transported into cells without losing its enzymatic activity. Furthermore, this method employs relatively small amounts of cationic polymer and is not limited to cationic polymers of large molecular size.

Perhaps even more important is the fact that this method is also effective with small molecules which are excluded or poorly transported into cells as long as those molecules can be covalently bonded to a cationic polymer. Thus, the method is capable of providing dramatically increased cellular transport of molecules such as drugs, co-factors, nucleotides, nucleotide analogues, etc.

In many cases, a very important advantage can be gained by using selected cationic polymers, such as poly-L-lysine and poly-L-arginine, which are excellent substrates for physiologic proteolytic enzymes present in mammaliam cells. This means that these cationic polymers, after having served as a transport carrier, can be digested or otherwise broken down inside the cells into normal physiologic by-products.

DESCRIPTION OF PREFERRED EMBODIMENTS

Figure 1:
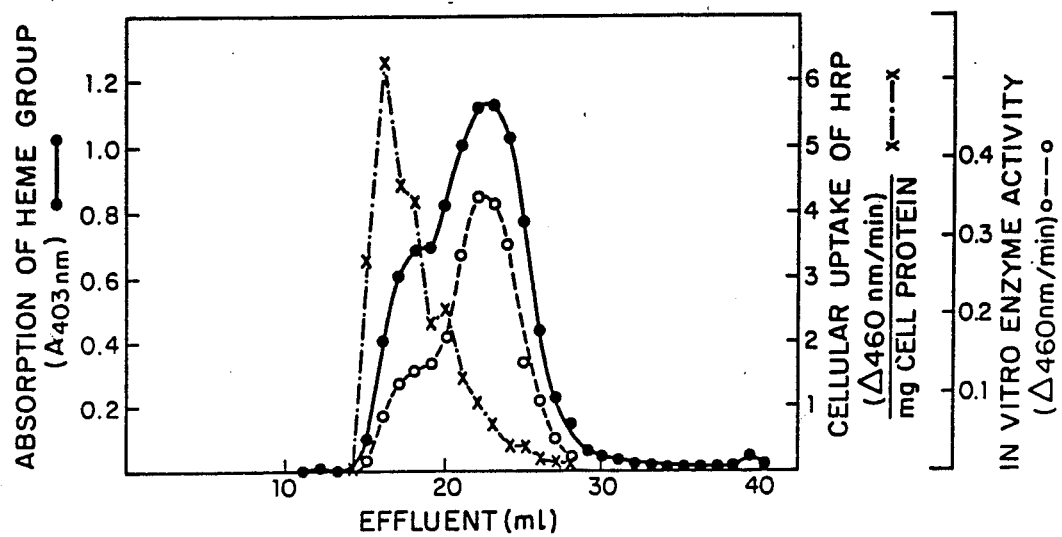
FIG. 1 contains several plots of data obtained from consecutive elution fractions exiting from a chromatographic column loaded with a reaction mixture of horseradish peroxidase (HRP), poly-L-lysine (PLL) and carbodiimide reagent which plots represent the HRP content and HRP enzymatic activity of consecutive fractions as well as their ability to enter cells.

There is a wide variety of molecules which can be covalently bonded to cationic polymers according to this invention to increase cellular uptake thereof. Included are certain macromolecules such as peptides, including oligopeptides, polypeptides and glycopeptides; proteins, including glycoproteins and lipoproteins; polysaccharides, including mucopolysaccharides; lipids, including glycolipids; nucleic acids, including RNA and DNA, either in soluble form or as part of supramolecular structures or organelles. Many small molecules are also suitable, including drugs, cofactors (e.g., cyanocobalamin), nucleotides, nucleotide analogues, etc., which are either excluded or only poorly transported into cells. In fact, it is believed that suitable conjugates can be formed for any molecule excluded from cells or only poorly transported into cells and which can be covalently bound to a cationic polymer. It is recognized, of course, that every molecule is probably transported into cells in some exceedingly small quantity and the term "excluded" is used herein in a functional sense rather than an absolute quantitative sense.

It is particularly noteworthy that biologically active enzymes can be covalently bonded to cationic polymers without losing their biological activity. This means that the intracellular content of biologically active enzymes can be increased by increasing their membrane transport, as illustrated by Examples 6–10, below.

Molecules which are excluded from cells are usually those normally excluded because of their charge pattern, size, or for other physico-chemical reasons. This method also applies, however, to molecules which are not normally excluded but become excluded because of mutations. Such mutations may lead either to the loss of a transport mechanism e.g., certain forms of drug resistance, as illustrated by Examples 14, 15, 23, 25, 27 and 28 below, or to the loss or impairment of a receptor site on cells (e.g., certain forms of familial hypercholesterolemia) or to the loss or impairment of a recognition marker on the molecules (e.g., certain mucopolysaccharidoses).

As used herein, the term "cationic polymer" means a polymer or macromolecule containing positively charged groups sufficient to enhance cellular uptake of molecules covalently bound to it. Such polymers include homopolymers and copolymers (random and block); linear, branched and crosslinked polymers; and synthetic and naturally occurring polymers.

Typically, although not exclusively, the positively charged groups are primary, secondary or tertiary amines which ionize at or around neutral pH. Such amine groups might be present as: amino groups in side chains as in poly(amino acids); amino groups included in a polymer backbone as in poly(amines); or amino substituents added to an uncharged polymer, such as result in dextran substituted with diethylaminoethyl groups. Polymers containing other positively charged groups, such as quaternary amines, the sulfur group in S-methyl methionine, etc., would also be suitable.

The preferred cationic polymers are cationic poly(amino acids), such as poly-L-lysine, which can be represented by the structural formula

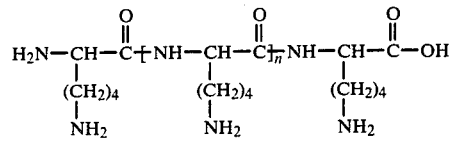

wherein n is an integer of 5 to 2000. A detailed description of poly(amino acids) is given in the following literature reference, the teachings of which are hereby incorporated by reference: Fasman, G. D., "Poly-α-amino Acids", Marcel Dekker, Inc., New York (1967).

Specific poly(amino acids) which are suitable include, but are not limited to, poly-L-lysine, poly-L-ornithine, poly-L-arginine, poly-L-homoarginine, poly-L-diaminobutyric acid, poly-L-histidine, the D-optical isomers thereof and copolymers thereof. Copolymers may include non-cationic amino acid residues. Cationic poly(amino acids) are preferred because of the outstanding enhancement in cellular uptake which they provide. Additionally, it is often desirable to employ cationic polymers which are digested by proteolytic enzymes present in mammaliam cells, and some poly(amino acids), such as, for example, poly-L-lysine and poly-L-arginine, provide this capability.

There are other classes of cationic polymers which are suitable in addition to poly(amino acids). These include polymers with neutral or anionic backbones to which cationic groups have been bonded, as in the case of substituted polysaccharides (e.g., diethylaminoethyl dextran), substituted cellulose, substituted copolymers of ethylene and maleic anhydride, substituted lactic or glycolic acid polymers, etc. Polyamines, such as for instance, poly(vinyl amine), or other cationic synthetic polymers, are also suitable. See Examples 9 and 10 below.

Certain positively charged, naturally occurring macromolecules also serve as suitable cationic polymers. Specific examples include protamines and histones, such as those found to increase cellular uptake of albumin by their simple presence. See Ryser, H. J.-P. and Hancock, R., Science, 150, pp 501–3 (1965). Other endogenous cationic macromolecules, especially peptides, endowed either with high rates of cellular transport or with special carrier properties might be isolated, purified and used as a carrier or vector for a molecule or macromolecule to be transported, as illustrated by Examples 11 and 12 below.

In general, multiple positive charges present on a polymer or macromolecule will enhance cellular uptake of that molecule. In most cases, such multiple positive charges will give the molecule a net positive charge. In other cases, however, the multiple charges may form an adequate sequence in the primary structure, or an adequate spacial arrangement in the tertiary structure, or both, to cause enhanced cellular uptake, even though the molecule does not have an overall net positive charge. For example, a molecule containing a limited number of positive charges at various intervals in its primary structure may fold in a manner such that a cluster of positive charges will be positioned in the same spatial area of its tertiary structure. Alternatively, a copolymer of poly(amino acid) with a neutral or negative net charge may contain a functionally important cluster of positive charges. Therefore, when used herein, the term "cationic polymer" refers not only to a macromolecule which has an overall positive net charge, but also includes macromolecules which contain sequential portions or spatial arrangements of positive charges sufficient to confer on them the transport properties of cationic polymers having a positive net charge thereon.

Conjugation can be achieved by well-known chemical reactions. For example, carbodiimide coupling can be used to couple a carboxyl or phosphate group on the molecule to be conjugated with amino groups of a cationic polymer. Such reactions are described in the following articles, the teachings of which are hereby incorporated by reference: Halloran, M. J. and Parker, C. W., "The Preparation of Nucleotide-Protein Conjugates: Carbodiimides as Coupling Agents", J. Immunology, 96, 373 (1966); Carraway, K. L. and Koshland, Jr., D. E., "Modification of Proteins by Carbodiimide Reaction", Methods in Enzymology, Vol. 25B, p 616 (1972); Sheehan, J. C. and Hess, G. P., "New Method of Forming Peptide Bonds", J. Am. Chem. Soc., 77, 1067 (1955); and Kurzer, F. and DouraghiZadeh, K., "Advances in the Chemistry of Carbodiimide", Chem. Rev., 67, 107 (1967).

A typical conjugation reaction between a protein (P) and a poly(amino acid) (PAA) and employing a carbodiimide (CDI) catalyst can be illustrated as follows:

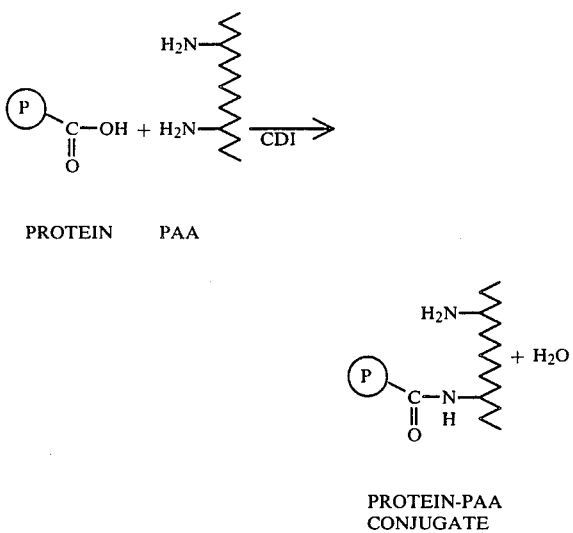

PROTEIN    PAA

PROTEIN-PAA
CONJUGATE such a conjugation is further illustrated by Examples 1 and 2 below.

Similarly, a typical carbodiimide conjugation reaction between a nucleotide formed from a purine or pyrimidine base and a poly(amino acid) can be illustrated as follows:

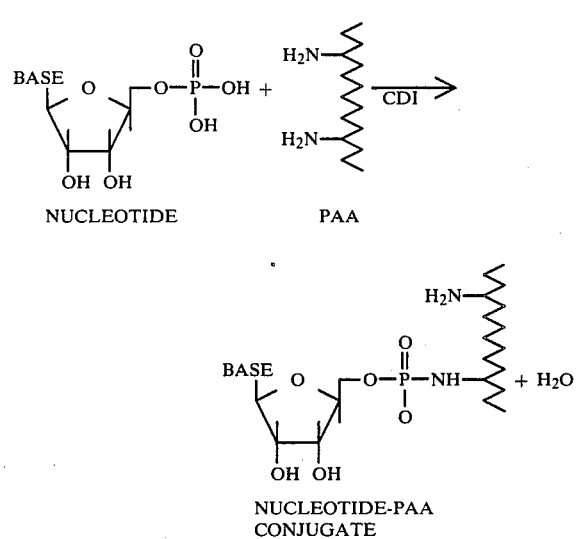

NUCLEOTIDE    PAA

NUCLEOTIDE-PAA
CONJUGATE

Such a conjugation is further illustrated by Example 15 below.

Conjugation can also be achieved for certain molecules by glutaraldehyde coupling between amino groups on conjugate molecules with amino groups on cationic polymers. Glutaraldehyde coupling is described in the following literature references, the teachings of which are also incorporated by reference: Avrameas, S. and Ternynek, T., "Peroxidase Labelled Antibody and Fab Conjugates with Enhanced Intracellular Pentration", Immunochemistry, 8, 1175–1179 (1971); Gonatas, N. K., Kim, S. U., Stieber, A. and Avrameas, S., "Horseradish Peroxidase-Lectin Conjugates", J. Cell Biol., 73, 1–13 (1977).

Depending upon the individual molecule to be conjugated, other modes of conjugation can be employed.

For instance, reductive periodation can be useful to conjugate daunomycin or other carbohydrate-containing molecules to any amino group-containing carrier. Such a reaction is described in the following literature reference, the teachings of which are incorporated by reference: Hurwitz, E., Levy, R., Maron, R., Wilchek, M., Arnon, R., and Sela, M. *Cancer Research*, 35, 1175, (1975).

Conjugation can also be achieved by using an intermediate molecule to link the drug to the carrier. Examples of such intermediate molecules, which might also be called spacer molecules, are oligopeptides, succinyl anhydride, and maleic anhydride. Conjugations which incorporate such spacer molecules may require a two-step reaction, in which the spacer molecule is first linked to the drug and the spacer-drug conjugate is then linked to the carrier. Thus, the term "covalently linked," as used herein, encompassed the use of such spacer molecules to bind the molecules to be transported to a cationic polymeric carrier.

Those skilled in the art will recognize, or be able to determine using no more than routine experimentation, other suitable conjugation mechanisms to covalently bond a specific molecule to be transported into cells to a specific cationic polymer chosen as a transport carrier The rate of cellular uptake of conjugates prepared according to this invention can be varied by varying the molecular weight of the cationic polymer, such as poly-L-lysine, employed to form the conjugate. Since it has been clearly demonstrated that the cellular uptake of labeled poly-L-lysine increases with its molecular weight (See Example 31 and FIG. 9), it can be expected that the same correlation will hold for other cationic polymers. When a drug is conjugated to poly-L-lysines of different molecular sizes, and provided the ratio of drug to unit weight of poly-L-lysine is constant, it can be seen that the level of cellular uptake of the conjugated drug will be determined by the molecular weight of the poly-L-lysine carrier. Hence the rate of cellular uptake of a conjugated drug can be predetermined by the molecular size of the homologous polymeric carrier. The rate of drug uptake, of course, also depends upon the number of drug molecules bound per unit weight of polymeric carrier.

Although the rate of cellular uptake increases with increasing molecular weight of cationic polymers such as poly-L-lysine, it does not follow that a comparably increased biological effect can always be seen. For example, the data obtained in Example 22 do not evidence an increasing biological effect for increasing molecular weight poly-L-lysine in MTX-PLL conjugates administered to CHO PRO$^{-3}$ MTX$^{RII}$ 5−3 cells. This indicates that other factors, such as intracellular degradation, affect biological activity.

The rate and extent of intracellular release of molecules which are covalently bonded to cationic polymers to form conjugates can also be controlled. This can be done by choosing polycationic polymeric carriers which differ in their susceptibility to intracellular digestion. It is known, for instance, that poly-L-lysine is very susceptible to trypsin and other proteolytic enzymes, while poly-D-lysine is not. This is illustrated in Example 36 and by FIG. 11. Thus, the carrier moiety of a drug-poly-L-lysine conjugate, once taken up by cells, can be expected to be digested by lysosomal proteases and to release free drug or active drug derivatives inside the cell. No such release is expected when the drug is conjugated to poly-D-lysine. This is demonstrated by the data of Examples 17 and 19 below. While methotrexate-poly-L-lysine (MTX-PLL) and methotrexate-poly-D-lysine (MTX-PDL) conjugate enter cells at comparable rates, as shown by Example 16, they have different biological effects: MTX-PLL strongly inhibits the growth of MTX-resistant cells; MTX-PLL has no such effect.

Carriers with intermediate susceptibility to proteolysis can be devised by using copolymers of amino acids or homopolymers of unnatural amino acids. An example of the latter is given in Example 36 and FIG. 12, and these show that ploy-L-homoarginine has a susceptibility to trypsin intermediate between that of poly-L-lysine and poly-L-ornithine.

Another method of controlling the intracellular release of molecules which are covalently bonded to cationic polymers is to modify the bonding procedure. One important modification is the introduction of a spacer molecule which is bonded on one side to the drug and on the other side to the carrier, as described above. When such a spacer molecule is an oligopeptide, for example, and as such susceptible to proteolytic digestion, it can be selectively digested inside the cell and the drug can be released even when the cationic carrier is not itself digestible.

Those skilled in the art will be able to take advantage of adjusting the level of cellular uptake as well as controlling the degree of intracellular digestibility and/or release by the above-described techniques by employing routine experimentation to determine the exact conjugate for their purpose.

It should be recognized that a macromolecule to be covalently bonded to a cationic polymeric transport carrier could itself be bonded to or complexed with one or more different small molecules, or could itself be carrying a core of small molecules. LDL and ferritin, for example, are examples of macromolecules which have such special transport properties.

Enhancement of cellular uptake of molecules normally excluded from cells or only poorly transported into cells can be utilized in many applications.

One area of application is the range of cancer treatments known generally as cancer chemotherapy, especially those involving drug-resistant cancers. Several important such chemotherapeutic applications are now described.

One significant reason for resistance to a chemotherapeutic drug is a deficiency in cellular uptake of that drug. A prototype drug known to encounter the development of such resistance is methotrexate. Methotrexate, a widely used cancer drug, is an analogue of folic acid and blocks an important step in the synthesis of tetrahydrofolic acid which itself is a critical source of 1-carbon compounds utilized in the synthesis of thymidylate. Thymidylate is a building block that is specific, and therefore especially critical, for DNA synthesis.

A conjugate formed between methotrexate and a cationic polymer, particularly a poly(amino acid) such as poly-L-lysine, would enhance cellular uptake of methotrexate and carry the drug into methotrexate-resistant tumor cells. A carbodiimide coupling reaction for forming a suitable conjugate between methotrexate and a poly(amino acid) can be illustrated as follows:

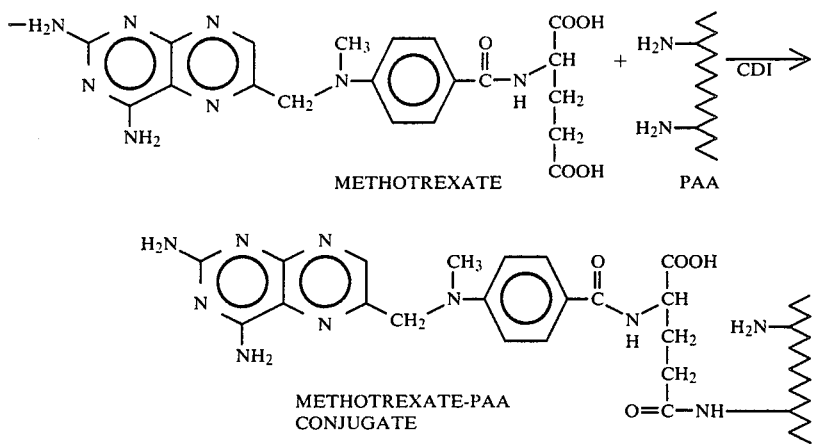

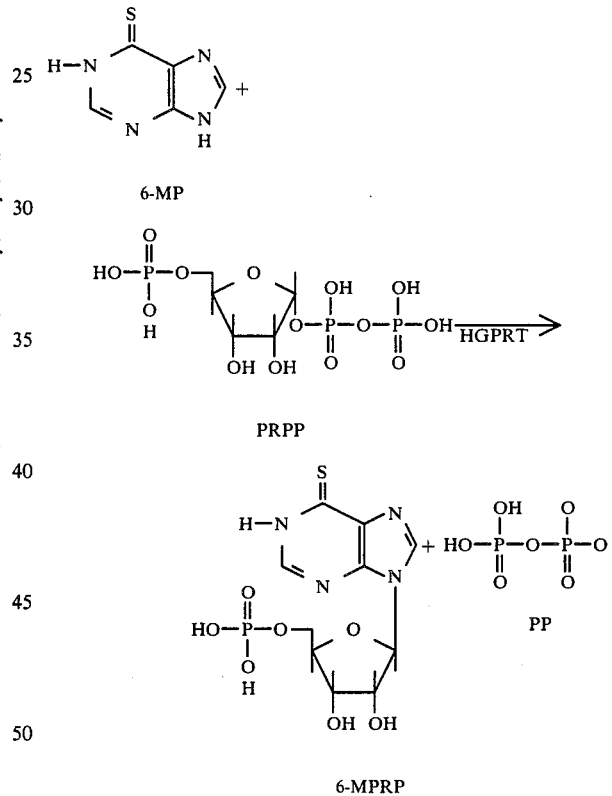

Although the above reaction is shown for purposes of illustration as involving one molecule of methotrexate conjugated through one of its carboxyl groups to one amino group of the carrier, in practice a number of molecules of methotrexate could be conjugated to a number of amino groups belonging to one molecule of cationic polymer, as illustrated by Example 13 below. Also, both carboxyl groups of each methotrexate molecule might be conjugated. Additionally, it should be understood that other reactions could be used to covalently bond methotrexate to a poly(amino acid) or to other cationic polymers, and that such reactions could include the incorporation of a spacer molecule as described above.

Methotrexate is one example of a drug to which cells can be or can become resistant because of deficiencies in cellular uptake, but there are others. For example, 5-fluorouracil, fluorodeoxyuridine, cytosine arabinoside, vinblastin, vincristin, daunorubicin, doxorubicin, actinomycin, and bleomycin all suffer from similar limitations, and conjugations of these to cationic polymers would also increase cellular uptake of these respective drugs into otherwise drug-resistant cells.

Another chemotherapeutic application for this invention arises in regard to those drugs to which cells become resistant due to inadequate intracellular activation of the drug. A prototype of a cancer drug to which tumor cells have beome resistant for lack of drug activation is 6-mercaptopurine (6-MP), a purine analogue. A common cause of tumor cell resistance to 6-MP is the loss of the enzyme hypoxanthine guanine phosphoribosyl transferase (HGPRT) which activates 6-MP into its corresponding nucleotide. Generally speaking, a nucleotide is the ribosyl- or deoxyribosyl phosphate of a purine or pyrimidine base, and more specifically in this case, a nucleotide analogue is the ribosyl- or deoxyribosylphosphate of a purine or pyrimidine base analogue. The HGPRT activation of 6-MP, to the nucleotide analogue, 6-mercaptophosphoribosylpurine (6-MPRP), requires the attachment of 5-phospho-D-ribose derived from 5-phospho-α-D-ribose pyrophosphate (PRPP) and can be illustrated as follows:

When the HGPRT enzyme is absent, 6-MP is without effect since the lethal form of the drug, i.e., the nucleotide analogue 6-mercaptophosphoribosyl purine (6-MPRP), is not synthesized following cellular uptake.

This resistance could be overcome if 6-mercaptophosphoribosyl purine itself could be introduced into the cell. Although this compound is commercially available, it has heretofore not been used therapeutically in cancer treatment because it is not adequately transported into living cells. Modification of this drug to covalently bond it to a cationic polymer would dramatically increase its ability to cross the cell membrane. An example of a carbodiimide conjugation to covalently bond 6-MPRP to a poly(amino acid) through a terminal phosphate group of the nucleotide analogue is given in Example 29 below and can be illustrated as follows:

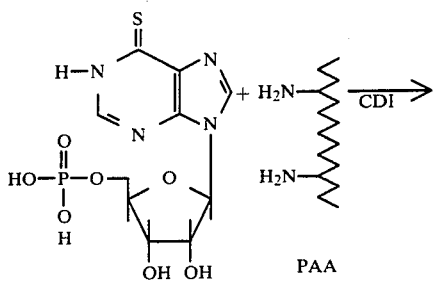

6-MPRP

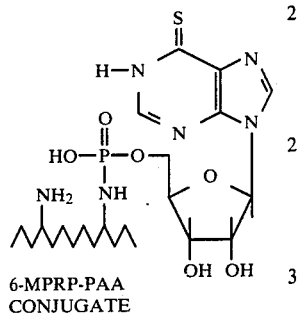

6-MPRP-PAA
CONJUGATE

A similar conjugation could be made using the terminal phosphate of 6-mercaptophosphoriboxyl purine triphosphate (6-MPRPPP). Similar conjugations could, of course, be made to cationic polymers other than poly(amino acids).

The same enzyme, HGPRT, also activates another cancer drug called thioguanine. A similar thioguanine-PLL conjugate could be formed to overcome resistance to this drug due to lack of the enzyme HGPRT.

There are also pyrimidine analogues which undergo activation to nucleotide analogues. These include 5-fluorouracil, 5-fluorouracil deoxyribose, 5-trifluoromethyl deoxyuridine, triacetyl-6-azauridine, cytosine arabinoside and adenosine arabinoside. The drug arabinoside, for instance, is an analogue of cytosine riboside, which is a physiological nucleoside. A nucleoside is a ribosylated or deoxyribosylated purine or pyrimidine base. Cytosine arabinoside is a nucleoside in which the normal pentose, i.e., ribose, has been replaced by an abnormal pentose, i.e., arabinose. The activation of cytosine arabinoside to the corresponding nucleotide requires the attachment of a phosphate, which is provided by adenosine triphosphate (ATP), the latter being converted to adenosine diphosphate (ADP). This reaction is catalyzed by the enzyme deoxycytidine kinase (DOCK), according to the reaction:

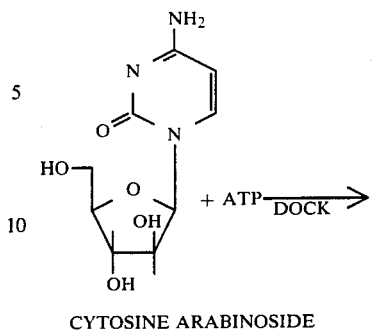

CYTOSINE ARABINOSIDE

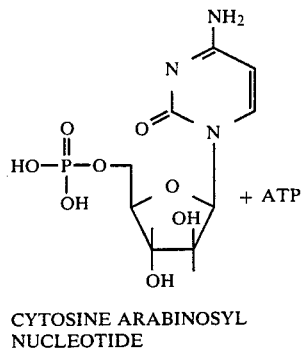

CYTOSINE ARABINOSYL
NUCLEOTIDE

There are known cases of drug resistance due to the loss of the enzyme deoxycytidine kinase. In such cases, cytosine arabinoside is without effect, since the lethal form of the drug, i.e., the cytosine arabinosylphosphate nucleotide, is not synthesized following cellular uptake of the drug. The activated form of this particular drug, and other similar drugs, is commercially available but has heretofore been therapeutically inefficient because it is not transported into living cells. However, cationic polymers such as poly-L-lysine can be coupled to the terminal phosphate of the cytosine arabinosylphosphate nucleotide, or other nucleotide analogues to enhance their cellular uptake.

Another form of drug resistance encountered in cancer chemotherapy is due to increased breakdown of a drug within the cell. One illustrative pathway of such inactivation is deamination of a pyrimidine base. It is known, for example, that cytosine arabinoside is more susceptible to deamination than its corresponding nucleotide. Thus, the direct introduction of a conjugate form of the nucleotide analogue cytosine arabinosyl phosphate would have the added advantage of being less susceptible to that form of inactivation and would thus be capable of overcoming a drug resistance that is due to increased drug destruction.

In addition to its utility in the cancer chemotherapeutic techniques described above, this invention also has significant application in aspects of cancer chemotherapy not necessarily related to drug resistance. For example, certain nucleotide analogues, which were found to be biochemically very effective in cell free systems, have never been developed as potential drugs because of their poor transport into cells. One such nucleotide analogue which is a very powerful inhibitor of DNA synthesis in cell free systems is dideoxyadenosine triphosphate. In cell free systems, this nucleotide analogue is incorporated into DNA, and once incorporated, blocks further elongation of the DNA molecule because of lack of the chemical group (3'-hydroxyl) required for polymerization. This compound cannot be used in the form of its precursor because cells are unable to synthesize a nucleotide of dideoxyadenosine. The nucleotide itself is not effective in therapy because it is not adequately taken up by cells. However, if this nucleotide were covalently bonded to a cationic polymer, such as poly-L-lysine, it could be transported into cells and function therein to kill tumor cells.

Still another application for this invention in cancer chemotherapy relates to a recently developed treatment for bone and muscle tumors wherein lethal doses of a drug, such as methotrexate, are administered, followed by administration of large doses of folinic acid. This is known as rescue therapy because the doses of methotrexate administered would kill the patient by totally depleting the stores of folinic acid if the patient were not saved after a suitable interval by administration of large doses of folinic acid. Folinic acid is taken up readily by normal cells and less so by tumor cells, and thus the ratio of tumor to normal cells killed is improved. Such improvement could be especially significant in drug resistant tumors with deficiencies in methotrexate transport, because such deficiencies often extend to the transport of folinic acid.

Comparable rescue procedures have not yet been worked out for drugs other than methotrexate, for instance, purine or pyrimidine analogues. In theory, they could be used in the course of therapy with 6-MP, or any of the other purine or pyrimide analogues mentioned previously, since the agents of rescue, i.e., normal nucleotides, are known and commercially available. The reason nucleotides have not been used for that purpose is, once again, that such nucleotides do not enter cells. If these nucleotides could be modified to penetrate into cells, they would immediately become available as rescue agents. The principle of this rescue treatment is to provide cells with the product of the enzymatic reaction that is blocked by the drug.

The rationale of this rescue procedure is that fast growing normal cells which are hit by the drug may respond more favorably than tumor cells to the antidote of the drug, i.e., the normal nucleotides. Empirical trials have shown that this premise is fulfilled for the folinic acid-methotrexate combination. Thus, there is good reason to assume that this premise would hold for the combination of purine or pyrimidine analogues and the corresponding normal nucleotide conjugates.

In addition to cancer chemotherapeutic applications, this invention can also be used in antimicrobial chemotherapy. For example, adenosine arabinoside, a nucleoside very similar to cytosine arabinoside, has been found to be very effective in the treatment of *Herpes Encephalitis*, a viral infection of the brain. To be effective, this drug must be activated in the cell to a full nucleotide, adenosine arabinosyl phosphate, which inhibits virus replication inside the cell. It is known that this drug has not been effective in all cases and it is probable that one reason for some of the failures has been drug resistance occurring either because this drug is taken up too slowly by infected cells, destroyed too rapidly inside the cells or not properly activated into fully effective nucleotides. Thus, the availability of a conjugate between adenosine arabinosyl nucleotide and poly-L-lysine or other cationic polymer would overcome such drug resistance.

This invention can also be used in areas of drug therapy other than cancer and antimicrobial chemotherapy, whenever deficiency in cellular drug transport appears to be the cause of a poor response to drug treatment. Such areas may include metabolic, endocrine, cardiovascular and other diseases.

Another area of application is the treatment of certain genetic diseases characterized by enzyme deficiencies. Several genetic diseases, especially storage diseases, are characterized by the absence or abnormality of specific lysosomal enzymes. In certain instances, these enzymes have deficient catalytic functions and fail to hydrolyze natural substrates present in lysosomes (e.g., sphyngolipidosis or glycogenosis). In other cases, especially in a mucopolysaccharidose called I-cell disease, enzymes have a normal catalytic function when tested in cell free systems but lack recognition markers responsible for their cellular uptake and for their normal distribution in diseased tissues. In both instances, it would be important to have available for possible therapy enzymes having an increased ability to enter into the diseased tissue. While the results of enzyme therapy in these diseases have so far been disappointing, some modest beneficial effects have been observed in a few instances. It can be anticipated that such partial success will be improved by using polycationic conjugates to these enzymes to enhance their cellular uptake.

Increased cellular uptake is also useful in areas employing protein or other macromolecules as biological markers. There are proteins, such as peroxidases, ferritin, cytochromes, catalases, etc., which are useful biological markers because they or their reaction products can be visualized within cells using either light or electron microscopy. Horseradish peroxidase, for example, is taken up by nerve endings and transported along the nerve axons to cells bodies, and this phenomenom has been used successfully to study neuronal connections in the central nervous system. Any method to increase cellular uptake or decrease intracellular breakdown of such biological markers will increase their usefulness in cell biology and/or neurobiology, since their effectiveness is usually limited by the ratio of their cellular uptake to their intracellular digestion.

This invention may also be useful in enhancing the cellular uptake of protein hormones or polypeptide hormones, such as insulin, especially when specific receptors for such hormones have been abolished or damaged by mutations or by diseases.

There are many other applications, of course. Some of these could include the cellular transport of chelating agent, immunological agents, interferon, growth stimulating or inhibiting factors or other molecules having biological functions.

The method could also be used to increase the cellular uptake of pesticides, including insecticides, etc.

The invention is further illustrated by the following specific examples.

EXAMPLE 1

COVALENT BONDING (CONJUGATION) OF POLY-L-LYSINE TO HUMAN SERUM ALBUMIN

Crystalline human serum albumin (HSA), poly-L-lysine (PLL) of average molecular weight of 6700, and 1-ethyl-3-(3-dimethyl-aminopropyl)carbodiimide (EDC) were dissolved in equal amounts of 20 mg each in 0.8 ml water. This solution was incubated at 25° C. for 3 hours with occasional shaking, and then loaded onto a Sephadex G100 chromatographic column which had been previously equilibrated with 0.01M phosphate buffered saline (PBS), pH 7.0. After loading, the column was eluted with PBS and fractions containing protein coming out of the column at and around the void volume were collected, pooled, concentrated to a volume of 1.0 ml, and then diluted with water to a volume of 10.0 ml. In order to remove unreacted HSA, this low salt solution was passed through a DEAE-Sephadex column.

A standard radioimmunoassay for HSA using anti-HSA-antibodies showed that the purified HSA-PLL conjugate had lost more than 99% of its initial HSA antigenicity, and thus that the preparation contained less than 1% unmodified HSA.

Acrylamide disc gel electrophoresis at pH 4.5 showed the absence of unmodified HSA. The normal HSA band was relaced by a set of bands, including some faster moving bands, as would be expected for highly positively charged conjugates. The complexity of the electrophoretogram may suggest some poly-L-lysine induced crosslinkage between HSA molecules.

EXAMPLE 2

COVALENT BONDING (CONJUGATION) OF POLY-L-LYSINE TO HORSERADISH PEROXIDASE

The procedures and reactants of Example 1 were used except that 20 mg of horseradish peroxidase (HRP) was substituted for HSA.

Upon acrylamide disc gel electrophoresis at a pH of 4.5, unreacted HRP displayed two close and sharp bands of equal intensity. These two bands were no longer visible in similar electrophoresis of the reacted HRP. Instead, these two bands were replaced by faster moving bands as would be expected for highly positively charged conjugates. There were also several new slow moving bands, suggesting that poly-L-lysine had caused some crosslinkage between HRP molecules.

The reaction solution was loaded onto a Sephadex G100 chromatographic column which had been previously equilibrated woth 0.01M PBS, pH 7. Elution with PBS gave the profile presented by the solid curve in FIG. 1. This curve was obtained by measuring the HRP concentration of successive 2 ml column elution fractions using the absorption of the heme group of HRP at 403 nm as a measure of concentration. As can be seen, there is a main peak corresponding to unreacted HRP and a shoulder located at the left of the main peak which shoulder corresponds to HRP-PLL conjugate. The fractions containing HRP-PLL conjugates, i.e. the equivalent of fractions 14 to 19 in FIG. 1, were pooled for use in the experiments described in Examples 6, 7 and 8. The enzymatic activity of the pooled HRP-PLL fractions was compared to that of unconjugated HRP using an assay employing dianizidine as an electron acceptor. In this assay the rate of color development at 460 nm ($\Delta A_{460\,nm}$/min) is used as an expression of enzymatic activity. It was found that the conjugation decreased the enzymatic activity of HRP by about 50 to 60%.

The enzymatic activity of each 2 ml fraction eluted from the column was determined using the same assay. The resulting data are shown as the dashed curve in FIG. 1.

Each elution fraction was also tested for transport into L929 fibroblast cells as described in Example 6, below. The resulting data are plotted as the partially dotted-partially dashed line in FIG. 1. These results show that the HRP-PLL fractions which enter cells most effectively are the first fractions eluted from the Sephadex column, hence the fractions containing the conjugates of largest molecular weight. Nevertheless, for the purpose of the experiments described in Examples 6, 7, and 8, the pooled HRP-PLL fractions were used.

EXAMPLE 3

CELLULAR UPTAKE OF HSA-PLL CONJUGATE COMPARED TO THAT OF UNMODIFIED HSA

In order to measure cellular uptake of HSA-PLL conjugate, conjugate was prepared using the procedure and reactants of Example 1 except that prior to reaction, some of the crystalline HSA was radioiodinated with $^{125}$I using the chloramin T-iodination procedure. See Sonoda, S. and Schlamowitz, M., "Studies of $^{125}$I Trace Labeling of Immunoglobin G by Chloramin-T," Immonochem, 7, 885 (1970). The measurement procedure for cellular uptake was similar to that previously described by Ryser in Lab. Invest., 12, 1009 (1963) and also in "Uptake of Protein by Mammalian Cells: An Underdeveloped Area," Science, 159, 390–6 (1968).

Monolayers of L929 mouse fibroblast cells were grown to confluence in Eagle's MEM medium supplemented with non-essential amino acids and 10% fetal calf serum. Cell cultures containing unmodified labeled HSA and cell cultures containing labeled HSA-PLL were incubated for 60 mins. at 37° C. in serum-free Eagle's MEM medium. After incubation, the monolayers of cells were washed twice with 5 ml of basal salt solution (BSS) at neutral pH and detached from the culture flask by brief exposure to trypsin. The detached cells were washed twice by centrifugation and resuspension in 5 ml BSS, once by resuspension in 5 ml heparin-containing BSS (5 mg/ml) and twice more with 5 ml BSS. The purpose of the wash in heparin-BSS was to remove HSA-PLL conjugates adsorbed to the cell surfaces by complexing the polycation part of the conjugate with the polyanion heparin. After this extensive washing procedure, these cells were dissolved in 1N sodium hydroxide. The protein concentration of this cell extract was determined by the method of Lowry as described by Lowry, O. H., Rosebrough, N. S., Farr, A. L., Randall, R. J., "Protein Measurement With The Folin Phenol Reagent", J. Biol. Chem., 193, pp 265–75 (1951).

Its $^{125}$I radioactivity was measured in a gamma scintillation counter and expressed as $\mu$g of $^{125}$I-HSA per mg of cell protein. This measurement was used as an expression of the cellular uptake of $^{125}$I-HSA and of its PLL conjugate during the 60 min. incubation. The concentration of $^{125}$I-HSA in either unmodified or conjugated form was 50 $\mu$g per ml of incubation medium throughout.

Two experiments were performed, and both included a direct comparison between cellular uptake of labeled HSA-PLL conjugate and labeled HSA. In addition, the first experiment included a measurement of cellular uptake of labeled $^{125}$I-HSA when administered to the cells in the presence of 10 $\mu$g/ml of PLL and the second experiment included a measurement of the cellular uptake of labeled $^{125}$I-HSA when administered to the cells simultaneously with 50 $\mu$g/ml of non-labeled HSA-PLL conjugate.

Cellular uptakes determined in this fashion were as follows:

| | Uptake In 60 Min. ($\mu$g/mg cell protein) | |
|---|---|---|
| | Experiment 1 | Experiment 2 |
| $^{125}$I-HSA-PLL | 5.2 | 5.9 |
| $^{125}$I-HSA | 0.41 | 0.60 |
| $^{125}$I-HSA + 10 $\mu$g/ml PLL | 0.41 | — |
| $^{125}$I-HSA + non-labeled HSA-PLL (50 $\mu$g/ml) | — | 0.77 |

As can be seen from the data, an approximate ten-fold enhancement of cellular uptake was achieved by conjugation of HSA to PLL. Free poly-L-lysine of the same molecular weight, i.e., 6700, when added in amounts comparable to the PLL content of the conjugate (10 $\mu$g/ml) did not cause any detectable enhancement of $^{125}$I-HSA uptake. Furthermore, when unlabeled HSA-PLL conjugate was added to unmodified $^{125}$I-HSA in the same amount (50 $\mu$g/ml), it did not cause any significant effect on the uptake of $^{125}$I-HSA. These results indicate that PLL serves as a carrier for the HSA protein covalently linked to it and significantly enhances transport of HSA through the cell membrane compared to transport of unconjugated HSA.

EXAMPLE 4

REVERSAL OF ENHANCED CELLULAR UPTAKE OF HSA-PLL CONJUGATE BY TRYPSIN-TREATMENT

The procedure of Example 3 was followed except that, prior to the experiments, part of the HSA-PLL conjugate was treated with trypsin. PLL is very sensitive to trypsin digestion, and enzymatic degradation of PLL in the conjugate would be expected to decrease the enhanced cellular uptake realized because of the PLL.

A 0.3 ml aliquot of HSA-PLL (1.5 mg/ml), prepared as in Example 1, was mixed with 30 $\mu$l of trypsin solution (0.25%) and incubated for 5 min. in a 37° C. water bath. The enzymatic reaction was stopped by diluting the 0.33 ml reaction mixture with 8.0 ml with Eagles' MEM medium containing 5% fetal calf serum (FCS). This dilution brought the HSA-PLL concentration to 54 $\mu$g/ml, which was roughly the same as in Example 3. Cellular uptake of the untreated HSA-PLL conjugate, of the trypsinized HSA-PLL conjugate, and of unconjugated HSA were measured following the procedure of Example 3. The results were:

| | Uptake in 60 min. ($\mu$g/mg cell protein) |
|---|---|
| $^{125}$I-HSA-PLL (no FCS) | 5.9 |
| $^{125}$I-HSA-PLL (+5% FCS) | 6.2 |
| $^{125}$I-HSA-PLL (+trypsin and +5% FCS) | 3.2 |
| $^{125}$I-HSA | 0.6 |

As can be seen from the data, trypsin treatment of the HSA-PLL conjugate decreased its uptake by approximately 50% when compared to the uptake of the non-trypsinized HSA-PLL conjugate. This indicates that the enhancement of uptake is determined by the PLL-content of the HSA-PLL conjugate, and further trypsinization would have been expected to further decrease enhancement. The data also indicate that the 5% fetal calf serum used to terminate trypsinization did not, by itself, modify the cellular uptake of the HSA-conjugate. The figures obtained for the cellular uptake of HSA-PLL and HSA are in close agreement with the data of Example 3.

EXAMPLE 5

REVERSAL OF ENHANCED CELLULAR UPTAKE OF HSA-PLL CONJUGATE BY CARBAMYLATION OF THE AMINE GROUP OF THE PLL MOIETY

The procedure of Example 3 was used, except that part of the HSA-PLL conjugate was first treated in the following manner.

One ml of $^{125}$I-HSA-PLL solution containing 1.5 mg conjugate per ml in phosphate buffered saline (PBS), pH 7, was mixed with 16 mg potassium cyanate and then incubated at 25° C. for 24 hours. After this, the solution was dialyzed extensively against PBS. More than 90% of the total protein and of the $^{125}$I radioactivity was recovered after dialysis. This procedure is known to carbamylate all $\alpha$- and $\epsilon$-amino groups of PLL and thus to abolish the positive charge of PLL at neutral pH. See Stark, G. R., "Modification of Proteins with Cyanate," *Methods Enzymol.*, 25B, 579 (1972).

Using the procedure of Example 3, the cellular uptake of $^{125}$I-HSA, $^{125}$I-HSA-PLL, and carbamylated $^{125}$I-HSA-PLL were measured at equal concentrations (50 $\mu$g/ml). The results were:

| | Uptake in 60 min. ($\mu$g/mg cell protein) |
|---|---|
| $^{125}$I-HSA-PLL | 5.02 |
| $^{125}$I-HSA-PLL-CARB. | 0.51 |
| $^{125}$I-HSA (control) | 0.44 |

As can be seen from these data, the uptake of $^{125}$I-HSA-PLL was increased compared to that of $^{125}$I-HSA by a factor of ten-fold, but carbamylation of the HSA-PLL conjugate abolished this enhancement and brought the cellular uptake back to control levels. This demonstrates that the enhanced uptake of HSA-PLL is due to the positive charges of the $\epsilon$-amino groups of the PLL-moiety in the conjugate. The figures obtained for the cellular uptake of HSA-PLL and HSA are in agreement with those of Examples 3 and 4.

EXAMPLE 6

CELLULAR UPTAKE OF HRP-PLL CONJUGATE COMPARED TO THAT OF UNCONJUGATED HRP AND MEASUREMENT OF HRP ENZYMATIC ACTIVITY

The procedure of Example 3 was generally followed except that HRP and fractions of HRP-PLL obtained as described in Example 2 were employed instead of $^{125}$I-HSA and $^{125}$I-HSA-PLL, at a final concentration of 0.1 mg/ml. Following exposure to HRP and HRP-PLL, and after extensive washing, the detached cells were lysed in 0.05% Triton X-100, and the cell extract was used for the measurement of enzymatic activity of HRP in an assay employing dianizidine as an electron acceptor. The rate of color development measured at 460 nm ($\Delta A_{460 \, nm}$/min) was used as an indication of enzymatic activity, and the enzymatic activity measured in the cell extract was used as an expression of cellular uptake. The cellular uptake of enzyme following exposure of cells to single fractions of HRP-PLL (single fractions are described in Example 2 above) is shown in FIG. 1, as the dashed-dotted line. The cellular uptake of enzyme following exposure of cells to HRP or to the pooled HRP-PLL fraction (described in Example 2) were as follows.

| Enzyme concentration in medium (μg/ml) | Cell-associated peroxidase activity (ΔA₄₆₀ nm/min/mg cell protein) after exposure to: | |
|---|---|---|
| | HRP | HRP-PLL |
| 1500 | 1.55 | — |
| 150 | 0.14 | — |
| 15 | — | 7.33 |
| 1.5 | — | 0.30 |
| 0 | (No measurable endogenous activity) | |

As can be seen from these data, extracts of cells exposed to 15 μg/ml HRP-PLL had 4.73-times more activity than extracts of cells exposed to a 100-times higher, and 43.1 times more activity than extracts of cells exposed to a 10 times higher concentration of unconjugated HRP. If corrected for exposures at comparable concentrations, the cellular uptake of the 2 forms of peroxidase would thus differ by a factor of 473 and 431 respectively. When cells were exposed to 1.5 μg/ml HRP-PLL, cellular uptake was 2.1 times higher than in cells exposed to a 100-fold higher concentration and 0.194 times that of cells exposed to a 1000-fold higher concentration of native HRP. Corrected for exposure at equal concentrations, this corresponds to a 210- and 194-fold difference in cellular uptake between the 2 forms of HRP. There is a discrepancy between the overall enhancement obtained when using 15 and 1.5 μg/ml HRP-PLL as a basis of comparison. There are at least two possible explanations for this discrepancy, i.e., preferential losses of HRP-PLL during the measurement procedure and preferential digestion of HRP-PLL by lysosomes. Both would influence the measurements at low concentration of HRP-PLL more significantly. Thus, the factors of 473 and 431 appear more reliable as an index of enhancement. It should be noted that these values are based on measurements of enzymatic activity. Since the enzyme was only 40% active in the conjugated form, the index of enhancement for the cellular uptake of enzyme protein thus becomes 2.5×473, i.e., 1182-fold. The possibility must be considered that lysosomal digestion of HRP-PLL might first attack the PLL moiety of the conjugate and transiently reactivate the enzyme, although attempts to reverse the 60% loss of activity in vitro have shown only minimal reactivation.

EXAMPLE 7

CELLULAR UPTAKE OF HRP-PLL CONJUGATE COMPARED TO UNCONJUGATED HRP:CYTOCHEMICAL STUDY

To ascertain that the measurements of enzymatic activity reported in Example 6 express a true cellular uptake of HRP and its conjugate, monolayers of L929 fibroblast were processed for cytochemical staining and cellular localization of the HRP reaction product.

A. Cytochemical localization of HRP reaction product as observed by light microscopy Monolayers of L929 fibroblasts were incubated for various periods of time in serum-free Eagle's medium containing HRP and HRP-PLL conjugate in concentrations ranging from 1.5 to 150 μg/ml. The incubation procedure was as described in Example 3, except that cells were grown to non-confluent monolayers on glass cover slips made to fit the tissue culture tubes. The washing procedure was modified as follows: after exposure to HRP, the monolayers were rinsed twice with basal salt solution (BSS). After transferring the coverslips bearing the monolayers to clean tissue culture tubes, they were incubated for 5 minutes at 37° C. in Heparin-BSS (5 mg/ml), rinsed 3 more times with BSS and fixed for 20 minutes at 25° C. with 2.5% gluteraldehyde in 0.1M cacodylate buffer, pH 7.4. After 5 rinses with cacodylate buffer, the cells were stained for 10 minutes with 0.5 mg/ml diaminobenzidine solution in 0.05M tris buffer, pH 7.6, containing a final concentration of 0.01% $H_2O_2$. After 4 more rinses in tris-buffer, and a fifth rinse in cocodylate buffer, the monolayers were fixed for 60 min, at room temperature with 2% $OsO_4$ in 0.1M cacodylate buffer. After 4 further rinses in cacodylate, the monolayers were dehydrated and mounted on glass slides.

Light microscopic observation, and photomicrographs therefrom, revealed minimal staining of HRP reaction products in the monolayer exposed for 60' to 150 μg/ml conventional HRP. In contrast, monolayers exposed to 1.5, 5, and 15 μg/ml of HRP-PLL showed a marked and dose-related staining. Since the exposure to 1.5 μg/ml HRP-PLL gave markedly stronger staining than exposure to a 100X larger concentration of unmodified HRP, and since the enzymatic activity of the modified HRP was 50% of the control HRP, it can be concluded that the conjugation of HRP to PLL enhanced its uptake more than 200-fold.

B. Cytochemical localization of HRP-reaction product as observed by Electron Microscopy Monolayers of L929 fibroblasts were processed as described under Example 7A, except that the monolayers were grown on glass coverslips coated with a carbon-film. The monolayers were processed as described in Example 7A until the completion of osmium fixation and the four subsequent rinses. They were then stained overnight at 4° C. with 1% Uranylacetate, rinsed with distilled water, dehydrated and embedded in Epon. The carbon film with its cell monolayer detached from the glass and became part of the Epon bloc. Thin sections cut parallel to the plane of growth were observed in a Philips 300 Electron microscope. Electron microscopic pictures of cells exposed to HRP-PLL revealed horseradish peroxidase reaction product in the form of abundant dark, densely stained opacities localized within endocytotic vesicles, throughout the cytoplasm, including the paranuclear areas. In contrast, cells exposed to a 100-time greater concentration of conventional HRP, showed minimal amounts of stained reaction product. This finding proves that HRP-PLL conjugate are present within the cells following cellular uptake and confirms that the conjugation of HRP with PLL increases its cellular uptake by more than 200-fold.

It should be emphasized that this demonstration of the intracellular localization of the enzyme is based on its enzymatic activity inside the cell. Therefore, this demonstrates the possibility of dramatically increasing, by means of membrane transport, the intracellular content of a biologically active enzyme.

EXAMPLE 8

CELLULAR UPTAKE OF HRP-PLL CONJUGATE: REVERSAL OF ENHANCEMENT FOLLOWING TRYPSIN TREATMENT OF THE CONJUGATE

This experiment was carried out as described in Example 7A except that, prior to the experiment, part of the HRP-PLL conjugate was treated with trypsin. PLL is very sensitive to tryptic digestion and it was expected that enzymatic degradation of the PLL moiety of the conjugate would decrease its cellular uptake. A 0.3 ml aliquot of HRP-PLL containing 0.85 mg/ml was incubated for 5 minutes in a 37° C. water bath in presence of 30 μL of trypsin (0.25%). The enzymatic reaction was stopped by 1:500 dilution with serum free growth medium to reach a final concentration of 1.5 μg HRP/ml. The cellular uptake of the trypsinized HRP-PLL was compared with that of the corresponding nontrypsinized preparation used at the same concentration (1.5 μg/ml). Cells exposed to the trypsinized conjugate showed no sign whatever of intracellular HRP reaction product when observed under the light microscope. In contrast, cells exposed to 1.5 μg/ml of HRP-PLL showed an amount of reaction product which was higher than that seen with amounts of 150 μg/ml unconjugated PLL. This result is consistent with that of Example 4 and demonstrates that the enhanced uptake of the HRP-PLL conjugate is indeed caused by the PLL-moiety of the conjugate. The experiment also confirms the difference in uptake of HRP and HRP-PLL noted in Example 7A.

EXAMPLE 9

COVALENT BONDING OF POLY(VINYLAMINE) TO HORSERADISH PEROXIDASE

The procedures and reactants of Example 2 were used except that poly(vinylamine) (PVA) of an average molecular weight of 20,000 was substituted for PLL. The weight of each of HRP, PVA and EDC were also reduced from 20 mg to 5 mg and the reaction volume from 0.8 ml to 0.4 ml.

The reaction product was loaded onto a Sephadex G-100 chromatographic column (1.2×38 cm), equilibrated with phosphate-buffered-saline (PBS) and the column was eluted with PBS. Each 1 ml fraction was collected. Measurement of HRP activity in each fraction revealed a sharp and complete separation of two enzymatically active peaks, the second of which corresponded to native unreacted HRP. The first peak, eluting at void volume, corresponded to HRP-PVA, and was pooled. It showed slight turbidity indicating that the HRP-PVA conjugate is less soluble in PBS than the native enzyme. Protein concentration of the pooled HRP-PVA fraction was determined by the method of Lowry et al.

EXAMPLE 10

CELLULAR UPTAKE OF HRP-PVA CONJUGATE COMPARED TO THAT OF UNCONJUGATED HRP, AND COMPARISON OF CELLULAR UPTAKE OF PVA- AND PLL-CONJUGATES OF HRP

The procedure of Example 6 was generally followed except that the pooled fraction of HRP-PVA obtained as described in the preceding example was used in addition to the pooled HRP-PLL fraction obtained as described in Example 2. The cellular uptakes of HRP-PVA and HRP-PLL were measured in the same manner. Following exposure to HRP, or one of its two conjugates, the monolayers of L 929 mouse fibroblasts were washed and detached and the detached cells were washed as described in Example 3. The cells were then lysed and the cell extract used for measurement of enzymatic activity of HRP as described in Example 6. The cell-bound HRP activities following a 60-minute exposure to HRP, HRP-PVA and HRP-PLL were as follows:

| Enzyme Concentration in medium (μg/ml) | Cell-Associated Peroxidase Activity ($\Delta A_{460\,nm}$/min/mg cell protein) after exposure to: | | |
|---|---|---|---|
| | HRP | HRP-PVA | HRP-PLL |
| 15 | 0 | 10.5[a] | 5.6 |
| 1.5 | 0 | 2.5 | (0.30)[b] |

[a]Some cell lysis was observed at this HRP-PVA concentration suggesting cellular toxicity. No such effect was seen at 1.5 μg/ml.
[b]Result taken from the Table of Example 6 for comparison.

As can be seen from these data, conjugation of HRP to PVA, MW 20,000, markedly increases the cellular uptake of enzymatically active HRP by L 929 cell monolayers. This increase is greater than that obtained with comparable amounts of HRP-PLL, especially at the lower concentration. This example demonstrates that conjugation of an enzyme to a cationic polymer other than a peptidic polymer can be at least as effective in enhancing the cellular uptake of active enzyme than conjugation to a cationic poly(amino acid).

To ascertain that the measurement of enzymatic activity reported in this example express a true cellular uptake of HRP-PVA, monolayers of L929 cells, exposed to HRP and HRP-PVA as described above, were processed for cytochemical staining and for cellular localization of the HRP reaction product as described in Example 7A. Light microscopic observations and photomicrographs therefrom confirmed that the differences in the enzymatic activity reported here express a true cellular uptake of HRP-PVA.

EXAMPLE 11

COVALENT BONDING OF A CATIONIC TETRAPEPTIDE (TUFTSIN) TO HUMAN SERUM ALBUMIN (HSA)

Tuftsin is a cationic tetrapeptide known to stimulate phagocytosis in leucocytes by interacting with a specific membrane receptor. See Najjar, V. A. and Nishoka, K. *Nature*, 228, 672–673 (1970); and, Tzehoval, E. et al., *Proc. Nat. Acad. Sci. U.S.A.*, 75, 3400–3404 (1978).

The procedure and reactants of Example 1 were used except that tuftsin was substituted for PLL, and that the weights of reactants and the reaction volume were modified as follows: 6 mg $^{125}$I-HSA and 5 mg tuftsin were dissolved in 0.3 ml PBS to which 10 mg EDC was added. This solution was mixed and kept in the dark at room temperature for 16 hours, after which the reaction was stopped by dilution with PBS to 1.0 ml. This solution was dialyzed at 4° C. in 1L PBS for 48 hours (one change of PBS at 24 hours) and recovered. There was total recovery of soluble radioactivity.

EXAMPLE 12

CELLULAR UPTAKE OF HSA-TUFTSIN CONJUGATE COMPARED TO THAT OF UNMODIFIED HSA

The procedure of Example 3 was generally followed except that the dialyzed solution of $^{125}$I-HSA-tuftsin obtained as described in Example 11 was substituted for $^{125}$I-HSA-PLL. The concentration of $^{125}$I-HSA in free and conjugated form was 50 µg/ml of incubation medium throughout. Cell-bound activity was measured after 1 and 60 minutes of incubation and the difference (60-1 min) was considered to represent net uptake. The results were:

|  | Uptake (CPM/mg cell protein) | | | Enhancement (multiple of control) |
| --- | --- | --- | --- | --- |
|  | 1 min. | 60 min. | 60-1 |  |
| $^{125}$I-HSA | 164.9 | 391.6 | 226.7 | 1 |
| $^{125}$I-HSA-Tuftsin | 883.2 | 2126.8 | 1243.6 | 5.5× |
| $^{125}$I-HSA-Tuftsin and 50 µg/ml Tuftsin | 646.4 | 1657.2 | 1010.8 | 4.6× |

As can be seen from these data, an approximate 5-fold enhancement of cellular net uptake was achieved by conjugating $^{125}$I-HSA to tuftsin. The addition of 50 µg/ml of tuftsin to the 50 µg/ml of $^{125}$I-HSA-Tuftsin conjugate decreased the net uptake of conjugate by approximately 20%, indicating moderate competition of the two compounds for membrane binding and uptake. These results indicate that the cationic tetrapeptide tuftsin, despite its small size, can serve as a carrier for the HSA covalently linked to it, and can enhance the transport of HSA through the cell membrane. The evidence of competition between tuftsin and HSA-Tuftsin suggests that the enhancement is related to binding of the tuftsin-moiety of the conjugate to tuftsin receptors at the cell surface.

EXAMPLE 13

COVALENT BONDING (CONJUGATION) OF POLY-L-LYSINE (PLL) TO METHOTREXATE (MTX) AND TO H$^3$-METHOTREXATE (H$^3$-MTX)

Methotrexate (MTX) was obtained from Sigma Chemical Co., St. Louis, Mo., and $^3$H-methotrexate (H$^3$-MTX) sodium salt (250 µCi, 18.5 Ci/m mol) was obtained from Amersham Co., Arlington Heights, Ill. Poly-L-Lysine (PLL) hydrobromide, MW 70,000, was obtained from Pilot Chemicals, Watertown, Ma. The carbodiimide reagent, 1-ethyl-3-(3 dimethylaminopropyl) carbodiimide was obtained from Sigma Chemical Co., St. Louis, Mo.

A 0.1 ml aliquot of methotrexate (MTX) solution (12 mg/ml, pH 7) was added to a small test tube containing 10 mg PLL, MW 70,000, in 0.5 ml H$_2$O. After thorough mixing, 20 mg carbodiimide reagent was added and the mixture was incubated for 2 hours at 25° C. with occasional shaking. The conjugate was then separated from the free MTX and other small molecules by Sephadex G-50 gel filtration. The MTX content of the various fractions was assayed by measuring their absorption at 257 nm in 0.1N NaOH. See Seeger, D. R., Cosulich, D. B., Smith, J. M. F. and Hultquist, M. E., *J. Amer. Chem. Soc.*, 71, 1753-1758 (1949). The conjugate came out of the column with the exclusion volume as a sharp symmetrical peak clearly separated from a minimal peak of unreacted MTX. More than 70% of the MTX used in the conjugation reaction was recovered in conjugated form. The conjugates of the pooled fraction had a MTX content of 8% on a weight basis corresponding to approximately 13 molecules per PLL molecule.

To prepare labeled MTX conjugate, a 0.1 ml aliquot of a MTX solution (20 mg/ml, pH 7) was added to a vial containing solid $^3$H-MTX sodium salt (250 µCi, 18.5 Ci per m mol). The final solution was adjusted to pH 7 with 1N HCl and was kept frozen as a stock $^3$H-MTX solution (62.5 mCi/m mole). The conjugation employed 0.05 ml of the $^3$H-MTX solution, added to a small test tube containing 5 mg PLL, MW 70,000, in 0.2 ml H$_2$O. Ten milligrams of carbodiimide reagent was then added and the reaction mixture was incubated at 25° C. with occasional shaking. After 2 hours, the mixture was passed through Sephadex G-50 column for purification as described above.

EXAMPLE 14

CELLULAR UPTAKE OF H$^3$-MTX AND H$^3$-MTX-PLL CONJUGATE

A Chinese hamster ovary cell line resistant to MTX (CHO Pro$^{-3}$ MTX $^{RII}$5-3) was obtained from Dr. W. F. Flintoft, University of Western Ontario, London, Ontario. A line of CHO wild-type cells from which the resistant cells had been derived (CHO WTT) was obtained from Dr. R. M. Baker, Massachusetts Institute of Technology, Cambridge, Ma.

The 2 lines of CHO cells were grown as monolayers in Corning culture flasks with a flat surface of 25 cm$^2$ (Corning Glass Works, Corning, N.Y.) in 5 ml Eagle's minimal essential medium, supplemented with pyruvate, vitamins and non-essential amino acids in the amounts contained in alpha medium.

The growth medium contained 10% fetal calf serum, penicillin (50 U/ml) and streptomycin (50 µ/ml). Cultures were started with 5×10$^4$ cells per flask.

Non-confluent monolayers were washed once with serum free growth medium and incubated at 37° C. in 5 ml serum free medium containing either $^3$H-MTX or $^3$H-MTX-PLL at a MTX concentration of 1×10$^{-6}$M. The specific activities of both $^3$H-MTX and $^3$H-MTX-PLL were 72.5 mCi per m mole. The radioactive medium was removed at various times and the monolayers were washed twice with 5 ml Earle's balanced salt solution. Cells were then detached from the flask by brief exposure to trypsin. The cell suspension was centrifuged at low speed and the cell pellet was washed twice more with 5 ml balanced salt solution. The final pellet was dissolved in 1.0 ml 1N NaOH and the protein content of each cell extract was determined by the method of Lowry. See Lowry, O. H., Rosebrough, N. S., Farr, A. L. and Randall, R. I., *J. Biol. Chem.*, 193, 265-275 (1951). A 0.5 ml aliquot of the remaining cell extract was mixed with 5 ml Aquasol (New England Nuclear, Boston, Ma.) and counted in a liquid scintillation counter.

Figure 2:
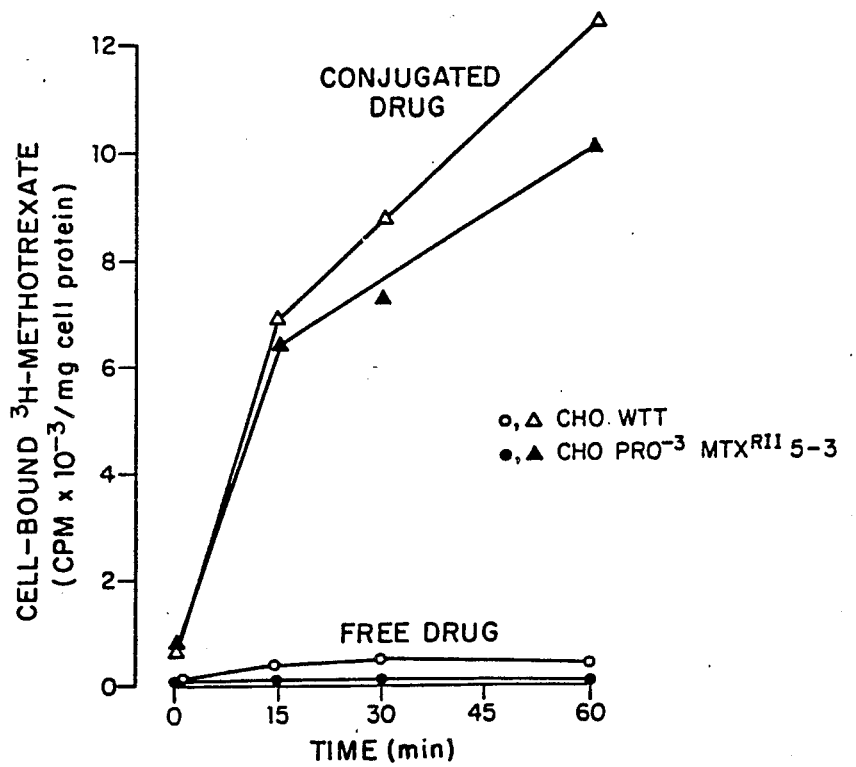
FIG. 2 is a plot illustrating the uptake of labeled methotrexate (MTX) and labeled methotrexate-poly-L-lysine conjugate (MTX-PLL) by transport-proficient and transport-deficient cells.

FIG. 2 shows the cellular uptake of free and conjugated methotrexate by the transport-proficient and transport-deficient cell lines as a function of time. The lower two curves represent the uptake of the free drug, and the upper two curves represent the uptake of the H$^3$-MTX-PLL conjugates. The conjugated drug is taken up much more readily than the free drug by both cell types. The uptake of free H$^3$-MTX by the transport-deficient cells is undetectable after 1 hour at the scale of FIG. 2, but is detectable in transport-proficient cells. When calibrated for comparable specific radioactivity of methotrexate, these measurements are in good agreement with those reported by Flintoff et al. See Flintoff, W. F., Davidson, S. V. and Siminovitch, L., *Somatic Cell Genet.*, 2, 245-261 (1976); Flintoff, W. F., and Saya, L., *Somatic Cell Genet.*, 4,143-156, (1978). The entry of free and conjugated drug differ not only in their magnitude but also in timecourse. In the case of the free drug, entry levels off after 30 minutes of exposure, while in the case of the conjugate, it is still increasing after 60 minutes. In transport-proficient cells, the accumulation of conjugated methotrexate is more than 20-fold greater than that of a free drug at 15 and 30 minutes, and more than 40-fold greater at 60 minutes. In transport-deficient cells, accumulation of conjugated drug is more than 200 times that of the free drug.

EXAMPLE 15

GROWTH INHIBITORY EFFECTS AND MTX AND MTX-PLL CONJUGATE ON CHO WTT, CHO PRO$^{-3}$ MTX$^{RII}$ 5-3 AND CHO PRO$^{-4}$ MTX$^{RII}$ 4-5 Cells The MTX transport-proficient and transport-deficient cell lines were grown for 24 hours. At that time either MTX or MTX-PLL were added to each flask to give final MTX concentrations ranging from $1 \times 10^{-9}$ to $1 \times 10^{-5}$M. After 2 days of exposure, the monolayers were refed with fresh medium containing the same drug concentrations. After 2 more days the monolayers were rinsed with balanced salt solution, detached by brief trypsinization (0.25% solution from Grand Island Biological Co.) and the suspended cells were counted in triplicate samples with a Coulter Counter. The cell count of random samples was verified using a hemocytometer. The results of these experiments are given in Table 1 and FIG. 3.

TABLE 1

| Exp. | MTX[1] Concentration in growth medium | Additions or Modifications | Number of cells × 10$^{-6}$ after 4 days in presence of | | |
|---|---|---|---|---|---|
| | | | No drug | MTX | MTX-PLL[2] |
| A | 0 | — | 4.06 | — | — |
| | $10^{-7}$ | — | — | 3.51 | 0.16 |
| | $10^{-7}$ | Free PLL 0.5 μg/ml | — | 4.60 | — |
| | $10^{-6}$ | — | — | 1.03 | 0.11 |
| | $10^{-6}$ | Free PLL 5.0 μg/ml | — | 1.63 | — |
| B | 0 | — | 5.95 | — | — |
| | $10^{-7}$ | — | — | 4.60 | 0.70 |
| | $10^{-7}$ | Exposure to trypsinized conjugate | — | — | 4.60[3] |

[1]Either in free or in conjugated form.
[2]Different preparations of MTX-PLL were used in Exps. A and B. They were prepared in similar fashion.
[3]Conjugate was briefly trypsinized before use.

As shown in Table 1, two different preparations of MTX-PLL used in different experiments were considerably more effective than the free drug in inhibiting the growth of MTX resistant cells. Free PLL at concentrations chosen to match the amounts present in the conjugates was added to media containing either $10^{-6}$ or $10^{-7}$M MTX and did not increase the effect of free MTX. This indicates that covalent linkage of the drug to PLL is necessary to increase its potency towards transport deficient cells. An aliquot of MTX-PLL was trypsinized in vitro prior to its use in order to hydrolyze the polymeric carrier component. It was then compared to the intact conjugate for its growth inhibitory effect on transport deficient cells. As can be seen from the last two lines of Table 1, the trypsinized conjugate behaved like free MTX and had little or no inhibitory activity at a concentration of $10^{-7}$M.

Figure 3:
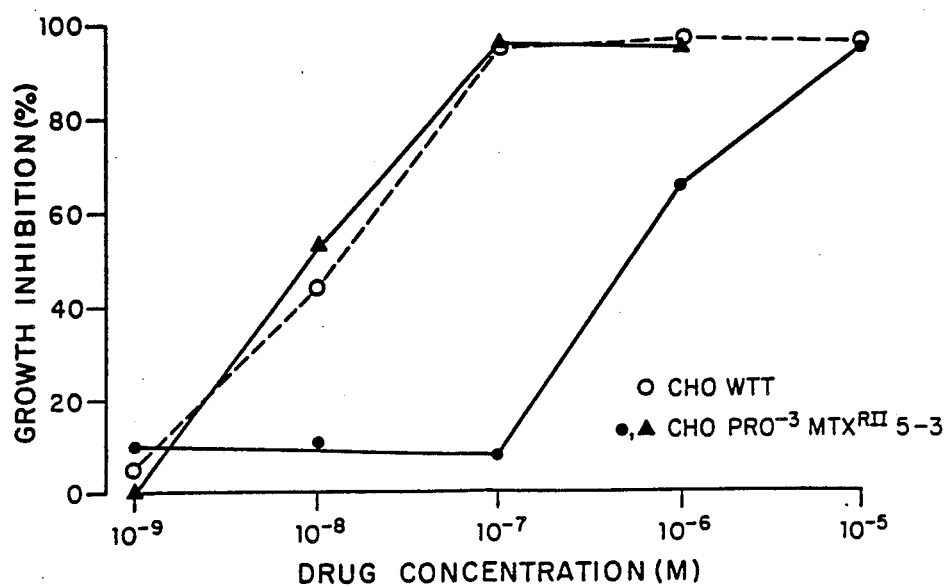
FIG. 3 is a plot illustrating the growth inhibitory effects of methotrexate (MTX) and methotrexate-poly-L-lysine conjugate (MTX-PLL) administered to cultures of transport-proficient and transport-deficient cells.

The inhibitory effect of MTX on transport proficient and transport deficient cells is compared in the dose-response diagram of FIG. 3. Approximately 100-times higher concentrations of free MTX were needed to cause comparable inhibitions in the transport deficient line as indicated by the horizontal distance between the corresponding curves. However, when transport deficient cells were exposed to the MTX-PLL conjugate, their dose-response curve was shifted to the left (solid curve) and become indistinguishable from that of free MTX-acting on drug sensitive cells (broken curve). This suggests that the drug conjugate can overcome the transport deficiency inherent to the mutant line. Free and conjugated drug had approximately identical effects on the drug-sensitive line.

A second MTX-resistant, transport-deficient, mutant of CHO, described by Flintoff as CHO PRO$^{-4}$ MTX$^{RII}$ 4-5, was tested in similar fashion. The level of resistance of both mutant lines to MTX was found to be of comparable magnitude and the resistance was overcome by MTX-PLL in comparable fashion.

EXAMPLE 16

CELLULAR UPTAKE OF $^3$H-MTX AND ITS PLL OR PDL CONJUGATE BY CHO PRO$^{-3}$ MTX$^{RII}$ 5-3 CELLS

This uptake experiment ws done on the CHO pro$^{-3}$ MTX$^{RII}$ 5-3 cell line by the same procedure as described in Example 14, except that $^3$H-MTX-PDL was also tested. $^3$H-MTX-PDL was prepared as described in Example 13 from poly-D-lysine hydrobromide, M.W. 60,000. The cells, after trypsinization, were washed once with 5 ml heparin solution (5 mg/ml) to eliminate any surface-bound polylysine since poly-D-lysine is not susceptible to trypsin digestion (See Example 34 and 36). The cells were then washed extensively with BSS and were dissolved in 1N NaOH. The results of the cellular uptake of $^3$H-MTX, $^3$H-MTX-PLL and $^3$H-MTX-PDL after 1 and 60 min exposures were as follows:

| | Cellular Uptake (cpm/mg cell protein) | | |
|---|---|---|---|
| | 1 min | 60 min | 60 min-1 min |
| $^3$H-MTX | 279 | 312 | 33 |
| $^3$H-MTX-PLL | 600 | 6689 | 6089 |
| $^3$H-MTX-PDL | 1106 | 7515 | 6409 |

This shows that there is no significant difference between MTX-PLL and MTX-PDL with regard to their cellular uptake.

EXAMPLE 17

COMPARISON OF THE GROWTH INHIBITORY EFFECTS OF MTX-PLL AND MTX-PDL ON CHO WTT AND CHO PRO$^{-3}$ MTX$^{RII}$ 5-3CELL LINES

The MTX transport proficient and deficient cell lines were treated with MTX or its conjugates as described in Example 15. The concentration of the drugs was $1 \times 10^{-6}$M of either free or conjugated MTX. MTX- PDL was prepared from poly-D-lysine hydrobromide with a molecular weight of 60,000 and was the same preparation as that used in Example 16. The growth inhibitory effects of MTX, MTX-PLL and MTX-PDL were as follows:

| Cell Line | Number of Cells × $10^{-6}$ After 4 Days in Presence of: | | | |
|---|---|---|---|---|
| | No Drug | MTX | MTX-PLL | MTX-PDL |
| WTT | 4.80 | 0.37 | 0.29 | 4.46 |
| Pro$^{-3}$ | 4.87 | 1.43 | 0.20 | 4.12 |

This shows that $1 \times 10^{-6}$M of MTX-PDL has no significant effect on either cell line. At this concentration, however, even free MTX can inhibit the growth of the resistant cells. Since there is no difference between the uptake of MTX-PLL and MTX-PDL by CHO Pro$^{-3}$ Mtx$^{RII}$ 5-3 cells, as shown in Example 16, and since the outstanding difference between these two conjugates is that the PLL conjugate is susceptible to proteolytic digestion while the PDL-conjugate is not, it can be concluded that the lack of biological effect of the MTX-PDL conjugate is due to the lack of intracellular digestion and of intracellular release of MTX or pharmacologically active MTX-derivatives.

EXAMPLE 18

INHIBITION OF DIHYDROFOLATE REDUCTASE IN VITRO BY MTX AND MTX-PLL

The effect of MTX and MTX-PLL on dihydrofolate reductase was measured in the assay described in Stanley, B. G., Neal, G. E. and Williams, D. C., Methods in Enzymology, eds. Colowick, S. P. and Kaplan, N. O. (1971) (Academic Press, New York) Vol. 18, pp. 771-779. Dihydrofolate reductase as well as the chemicals required for its assay were purchased from Sigma Chemical Co., St. Louis, Mo.

Figure 4:
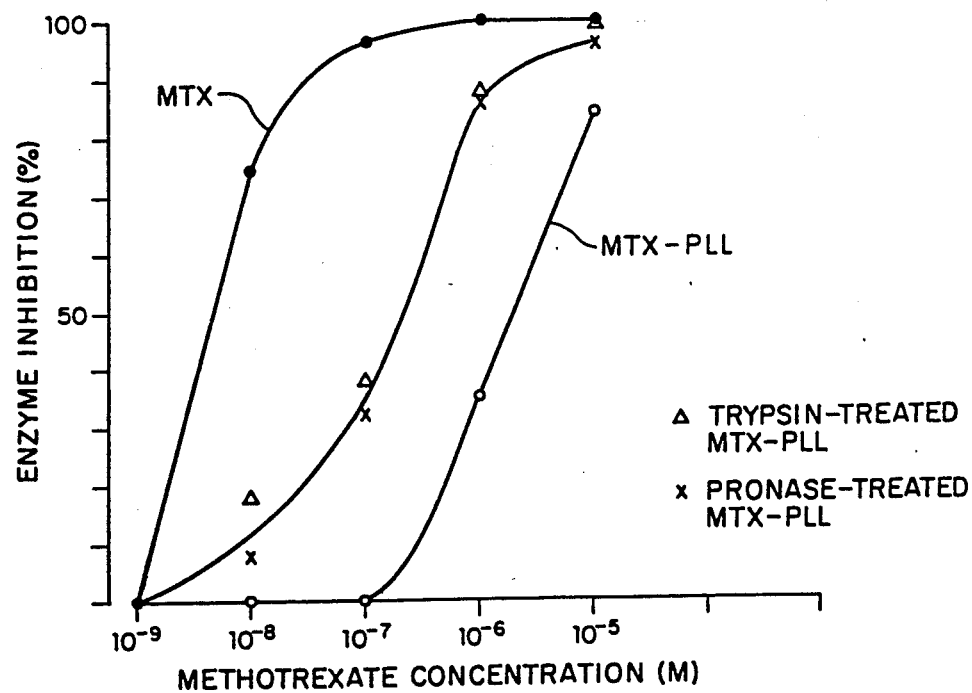
FIG. 4 is a plot illustrating the inhibitory effect of free methotrexate (MTX), methotrexate-poly-L-lysine conjugate (MTX-PLL) and partially digested conjugate on dihydrofolate reductase activity, in vitro.

The data are plotted in FIG. 4, and it can be seen therein that the conjugate did not show any inhibition of dihydrofolate reductase in vitro at MTX concentrations of $10^{-8}$ and $10^{-7}$M, while under the same assay conditions the MTX showed about 75% inhibition at $10^{-8}$M and about 95% inhibition at $10^{-7}$M. Prior treatment of the conjugate with 0.25 mg/ml trypsin or pronase partially restored the inhibitory effect on dihydrofolate reductase in vitro.

Since the MTX-PLL conjugate has a strong inhibitory effect on growing CHO cells as shown in Examples 15 and 17 above, it must be concluded that a restoration of inhibitory activity comparable to that shown in this example is occuring inside the cells under the action of intracellular proteolytic enzymes.

It can also be predicted that in vitro treatment of MTX-PDL with trypsin or pronase will not restore its inhibitory effect on dihydrofolate reductase in vitro.

EXAMPLE 19

DETECTION OF INTRACELLULAR DEGRADATION PRODUCTS OF $^3$H-MTX-PLL AND $^3$H-MTX-PDL IN CULTURED CELLS EXPOSED TO CONJUGATES

Methotrexate-resistant cells, Pro$^{-3}$MTX$^{RII}$ 5-3, were grown in a 75 cm$^2$ flask and approximately one day before reaching confluence, were exposed for 24 hours at 37° C. to $1 \times 10^{-6}$M of $^3$H-MTX-PLL and $^3$H-MTX-PDL. The labeled growth medium was then removed and the cell monolayers were washed twice with 15 ml buffered salt solution (BSS). The cells were detached from the flask by brief trypsinization and washed three times by low speed centrifugation in 5 ml BSS. The last cell pellet was dissolved in 1 ml of 1% sodium dodecylsulfate (SDS) in 0.01M phosphate buffer, pH 7. A small amount (0.2-0.3 mg) of unlabeled MTX was added to each pellet before cell lysis as a carrier for traces of $^3$H-MTX in the cell extract. The cell extract was then loaded onto a Sephadex G-25 column (1.5×24 cm) which had been quilibrated with SDS-phosphate-buffer and the column was eluted with the same buffer. Each 2-ml fraction was collected from the effluent of the column and 0.5 ml aliquots from each fraction were mixed with 5 ml Aquasol and counted in a liquid scintillation counter. The unlabeled MTX added to the cell extract as carrier was identified by measuring the absorbance of each fraction at 257 nm.

Figure 5:
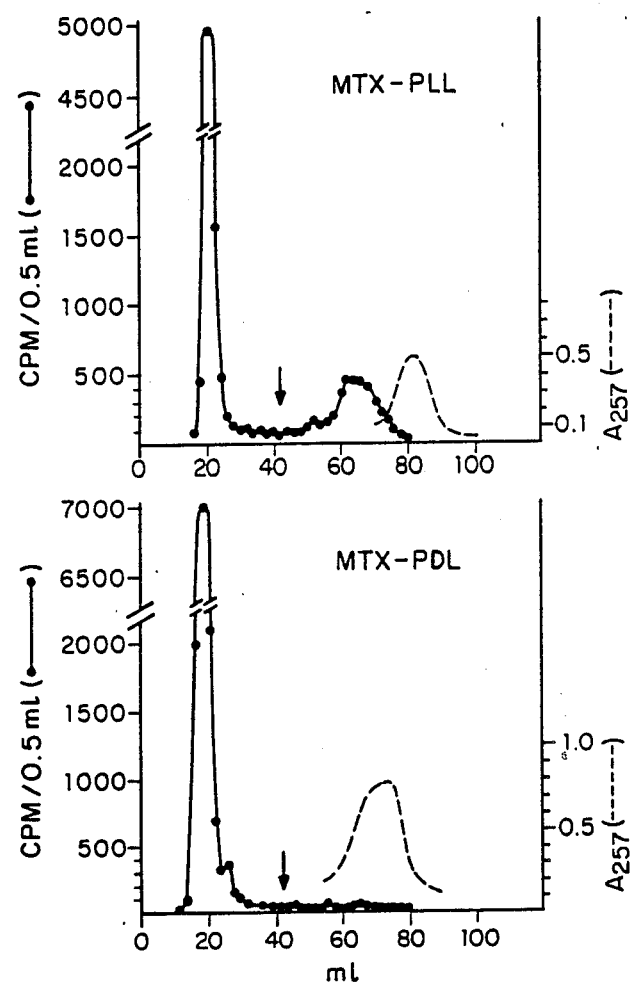
FIG. 5 illustrates elution profiles of intracellular degradation products of $^3$H-MTX-PLL and $^3$H-MTX-PDL conjugates.

FIG. 5 shows typical elution profiles of the extracts of monolayers exposed to $^3$H-MTX-PLL (upper panel) and $^3$H-MTX-PDL (lower panel). The arrows correspond to the total volume of the column. The solid curves show the radioactivity in each fraction, and the dotted curves indicate the unlabeled MTX added to the cell extract as carrier and internal marker. The cell extract from MTX-PLL treated cells shows a peak of radioactivity close to but not coincident with MTX. This peak, which represents about 25% of the total radioactivity in the cell extract, is believed to be a digestion product of MTX-PLL. No such peak is detected in the extract of cells exposed to MDX-PDL. The lack of such digestion product is consistent with the fact that PDL is not susceptible to hydrolysis by intracellular proteases. The conclusion that the small molecular peak of radioactivity represents an intracellular degradation product of $^3$H-MTX-PLL is further supported by experiments in which the $^3$-H-MTX-PLL conjugate was digested in vitro. When the conjugate was exposed sequentially for 20 min, at 37° C. to 0.25 mg/ml trypsin and protease and when the digest was loaded onto a Sephadex G-25 column comparable to the one used in this example, the elution pattern showed a peak of relative magnitude and of relative position comparable to the peak seen in the upper panel of FIG. 5.

These data indicate that neither intracellular nor in vitro digestion releases free MTX but released instead a small molecular adduct MTX. It is postulated that this digestion product is pharmacologically active and is responsible for the biologic effect of the MTX-conjugate. While the identification of this product is not yet completed, it is assumed that it represents lysyl- or dilysyl-MTX.

EXAMPLE 20

CELLULAR UPTAKE OF $^3$H-MTX-PLL IN THE PRESENCE OF AN EXCESS OF UNLABELED PLL

This uptake experiment was done using CHO PRO$^{-3}$ MTX$^{RII}$ 5-3 cells, following the same procedure as described in Example 14, except that the MTX concentration of $^3$H-MTX-PLL was $1 \times 10^{-7}$M and that cells were grown in larger culture flasks (75 cm$^2$) in order to obtain higher total radioactivities per monolayers. At a MTX concentration of $1 \times 10^{-7}$M, the conjugate contained 0.5 µg/ml of PLL of molecular weight of 70,000. The incubation was carried out in the presence and absence of 5 µg/ml of free unlabeled PLL of the same molecular weight. The cellular uptake of labeled conjugate, expressed as CPM/mg cell protein, was as follows:

| PLL Concentration (μg/ml) | | Cellular uptake of $^3$H-MTX-PLL (CPM/mg cell protein) | | |
|---|---|---|---|---|
| In Conjugate | Added in Unlabeled Form | 1 min | 60 min | 60 min–1 min |
| 0.5 | 0 | 58 | 701 | 643 (100) |
| 0.5 | 5 μg/ml | 54 | 573 | 519 (80) |

As revealed by these data, the addition of a 10-fold excess of unlabeled PLL to the medium decreases by 20% the cellular uptake of $^3$H-MTX-PLL. This result suggests that an excess of PLL, can compete with $^3$H-MTX-PLL for uptake, but only moderately so.

EXAMPLE 21

GROWTH INHIBITORY EFFECT OF MTX-PLL IN THE PRESENCE OF AN EXCESS OF PLL AND PDL

This experiment was done with CHO PRO$^-$$^3$MTX-$R^{II}$ 5-3 cells and the procedure of Example 15 was followed except that MTX was used only as conjugate, at only one concentration ($1 \times 10^{-7}$M), and that increasing concentrations of unconjugated PLL and PDL were added together with the MTX-PLL conjugate. The PLL content corresponding to a $1 \times 10^{-7}$M MTX concentration of MTX-PLL is 0.5 μg/ml. The number of cells per culture flask after a 4 day exposure to $1 \times 10^{-7}$M MTX-PLL was expressed as percent of control cells grown in absence of MTX-PLL. The results were:

| MTX-PLL ($1 \times 10^{-7}$ M) | Addition | (ug/ml) | Number of Cells (% of control) |
|---|---|---|---|
| − | − | | 100 |
| + | PLL | 0 | 19 |
| + | | 0.5 | 16 |
| + | | 1.0 | 52 |
| + | | 2.0 | 116 |
| + | | 3.0 | 118 |
| + | | 4.0 | 117 |
| + | PDL | 0 | 20 |
| + | | 0.5 | 25 |
| + | | 1.0 | 79 |
| + | | 2.0 | 112 |
| + | | 3.0 | 115 |
| + | | 4.0 | 114 |

These results show that addition of an increasing excess of PLL to the growth medium first decreases then totally abolishes the growth inhibitory effect of MTX-PLL. A marked decrease is seen already with a 2-fold excess (1.0 μg/ml) and total reversal is seen with a 4-fold excess (2.0 μg/ml). The same qualitative and quantitative pattern of protection was observed when PDL was added instead of PLL. As indicated in Example 17, PDL is not a suitable carrier for MTX because it is not susceptible to cellular hydrolases and therefore does not release pharmacologically active small molecular MTX-derivatives inside cells (see Example 19). Despite these differences, PDL is as effective as PLL in decreasing the growth inhibitory effect of MTX-PLL. As shown in Example 20, PLL competes only moderately with MTX-PLL for cellular uptake. It must be concluded therefore that the marked protective effect of PLL result from a competition with MTX-PLL at a level other than cellular transport. At the highest concentration of PLL and PDL, the number of cells per culture flask exceeds that of the control cultures. This appears to be due to the fact that PLL and PDL increase adhesion of growing cells to the tissue culture flasks.

EXAMPLE 22

GROWTH INHIBITING EFFECT OF MTX-PLL CONJUGATE OF DIFFERENT MOLECULAR WEIGHTS

Methotrexate (MTX) was conjugated with PLL of molecular weights of 3,100; 20,000; 70,000 and 130,000, using the procedure described in Example 13. These conjugates were purified by either Sephadex G-50 or Sephadex G-25 gel filtration. The amounts of MTX per mg of PLL were almost identical for all four conjugates. However, the concentrated solution of the conjugate of lowest molecular weight contained some aggregates. The stock solution of this conjugate was therefore filtered and its MTX concentration was measured prior to each experiment. The growth inhibitory effects of these four conjugates at a MTX concentration of $1 \times 10^{-7}$M was determined on CHO PRO$^-$$^3$MTX$^{RII}$ 5-3 cells as described in Example 15. The results were as follows:

| PLL M.W. of Added MTX-PLL | Number of Cells % of Control |
|---|---|
| Control (No MTX-PLL added) | 100 |
| 130,000 | 9.7 |
| 70,000 | 11.7 |
| 20,000 | 7.1 |
| 3,100 | 7.0. |

It is apparent from these results that, at a MTX concentration of $10^{-7}$M, no significant difference could be found in the growth inhibition caused by conjugates of PLL of molecular weights varying between 3,100 and 130,000.

It is of interest to relate these results with those of Example 31 which demonstrated that the cellular uptake of radioiodinated PLL increased with their molecular weight. The fact that no similar correlation is found between molecular weight and biological effect of MTX-PLL suggest that there must be factors other than cellular uptake which limit the biological effect of MTX-PLL conjugates. The most obvious other factor is the rate of intracellular release of pharmacologically active drug following cellular uptake. It can be postulated, therefore, that active MTX and/or active MTX-derivatives are more readily released following the uptake of small molecular MTX-PLL conjugates.

EXAMPLE 23

ANTITUMOR EFFECT OF MTX-PLL INJECTED INTRAVENOUSLY

The P 1798 S/B tumor, a cortisol-sensitive and methotrexate-resistant lymphosarcoma, was passaged subcutaneously in BALB/c male mice weighing between 20 and 25 g. Cell suspensions were made by teasing minced pieces of tumor through a stainless steel screen, and $1 \times 10^7$ cells were injected subcutaneously in the left scapular region.

The inoculation developed into a palpable tumor within 7-8 days and killed the animal on the average within 14 days. Following inoculation, mice were divided into 4 groups of 4 or 5 mice. One week or more after inoculation these groups were subjected to different treatments consisting of one daily injection of 0.2 ml of one of the following solutions: Group 1 (control), buffered saline; Group 2, PLL, (MW 2,700) 1.56 mg/ml in buffered saline: Group 3, MTX, 0.125 mg/ml in buffered saline; Group 4, MTX-PLL conjugate containing 0.125 mg/ml MTX and 1.56 mg/ml PLL (MW 2,700) in buffered saline.

In the first experiment, treatment was initiated on Day 12 after inoculation and consisted of a daily injection in the tail vein for 3 consecutive days. In the second experiment, the same treatment began on the 8th day after inoculation and was given for 4 consecutive days. All animals were sacrificed 1 day after the last injection. The subcutaneous tumors were carefully excised in toto and weighed. The results were:

| | Experiment No. 1 | | Experiment No. 2 | |
|---|---|---|---|---|
| Group | Mean Tumor Weight (g) | % of Controls | Mean Tumor Weight (g) | % of Controls |
| 1 | 4.40 ± 0.34$^a$ (4)$^b$ | 100 | 4.94 ± 0.13 (5) | 100 |
| 2 | 4.56 ± 0.45 (4) | 103 | 5.07 ± 0.08 (4) | 103 |
| 3 | 4.53 ± 0.28 (5) | 102 | 4.80 ± 0.50 (5) | 97 |
| 4 | 3.17 ± 0.32 (5)$^c$ | 71$^c$ | 2.47 ± 1.54 (5)$^d$ | 50$^d$ |

$^a$Mean ± SEM
$^b$Number of animals
$^c$P < 0.005 when compared to any other group
$^d$P < 0.001 when compared to any other group (includes 1 mouse that exhibited complete regression).

As can be seen from these data, the average tumor weight of animals receiving free MTX or PLL alone failed to show any reduction in either experiment. By contrast, the animals receiving MTX-PLL conjugate showed reductions to 71% and 50% of the control weight in experiments 1 and 2, respectively. These reductions are statistically highly significant, when compared to either one of the other 3 groups. The greater weight reduction seen in the second experiment is consistent with the fact that in the second experiment, treatment was begun 4 days sooner and continued for one more day than in experiment 1.

Two comparable experiments were carried out with a variant of the P 1798 lymphosarcoma known to be steroid-resistant and presumed to be MTX-sensitive. Treatment consisted of one daily intravenous injection for 4 consecutive days, and was begun on Day 11 and Day 12 post-inoculation in experiment number 1 and 2 respectively. All animals were sacrificed one day after the last injection. The results were:

| | Experiment No. 1 | | Experiment No. 2 | |
|---|---|---|---|---|
| Group | Mean Tumor Weight (g) | % of Controls | Mean Tumor Weight (g) | % of Controls |
| 1 | 5.35 ± 0.42$^a$ (3)$^b$ | 100 | 5.99 ± 0.26 (4) | 100 |
| 2 | 6.05 ± 0.52 (4) | 113 | 6.13 ± 0.31 (4) | 102 |
| 3 | 4.58 ± 0.31 (4) | 85 | 5.29 ± 0.40 (5) | 88 |
| 4 | 4.68 ± 0.26 (4) | 87 | 5.26 ± 0.11 (5) | 88 |

$^a$Mean ± SEM
$^b$Number of animals

These data show that in both experiments, the injection of free and conjugated MTX had comparable effects and caused a reduction of tumor weight between 85 and 88% of the control weight. These decreases are not statistically significant. The observation that administration of MTX-conjugate caused a lesser reduction of tumor weight than in the two experiments using MTX-resistant tumors suggests that the steroid resistant P 1798 tumor is partially resistant to MTX, for reasons other than defective MTX transport.

EXAMPLE 24

SURVIVAL EXPERIMENTS USING LYMPHOSARCOMA-BEARING MICE TREATED WITH MTX AND MTX-PLL CONJUGATE

Figure 6:
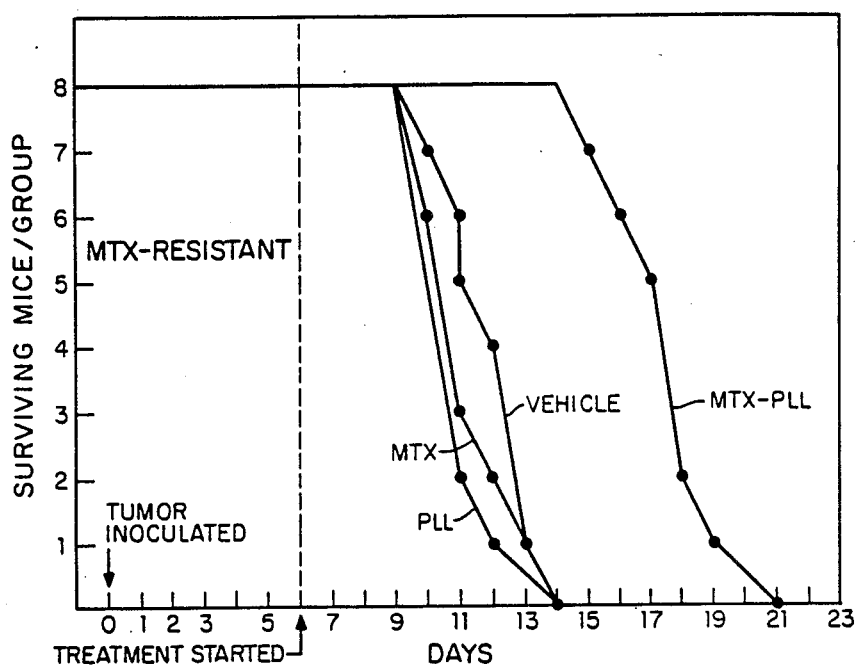

Four groups of 8 BALB/c mice were inoculated subcutaneously with $1 \times 10^7$ cells of P 1798 S/B lymphosarcoma, a MTX-resistant, steroid-sensitive tumor. Treatment consisted of one daily 0.2 ml injection in the tail vein beginning on the sixth day after inoculation, and was continued until the death of the animal. The first two groups of mice served as controls and received 0.2 ml of either buffered saline (Group 1) or PLL (MW 2,700), 1.56 mg/ml in buffered saline (Group 2). Group 3 received 1 mg/kg free MTX (0.025 mg/injection), and Group 4 received the same amount of MTX as Group 3, and the same amount of PLL as Group 2 in the form of MTX-PLL conjugate. The number of surviving animals in each group was plotted as a function of time (days) and is shown in FIG. 6. This Figure shows that the survival pattern of the two control groups is the same as that of Group 3, which received free MTX. In all three groups, the first death occurred on day 10 or 11 and the last survivor died on day 14. By contrasts, in the group receiving MTX-PLL, the first death occurred on day 15 and the last survivor died on day 21. Thus, the use of MTX-PLL conjugate prolonged survival by an average of 6 days. The longest survival measured from the initial treatment was 8 days in the group receiving free MTX and 15 days in the group receiving the MTX-PLL conjugate.

Figure 7:
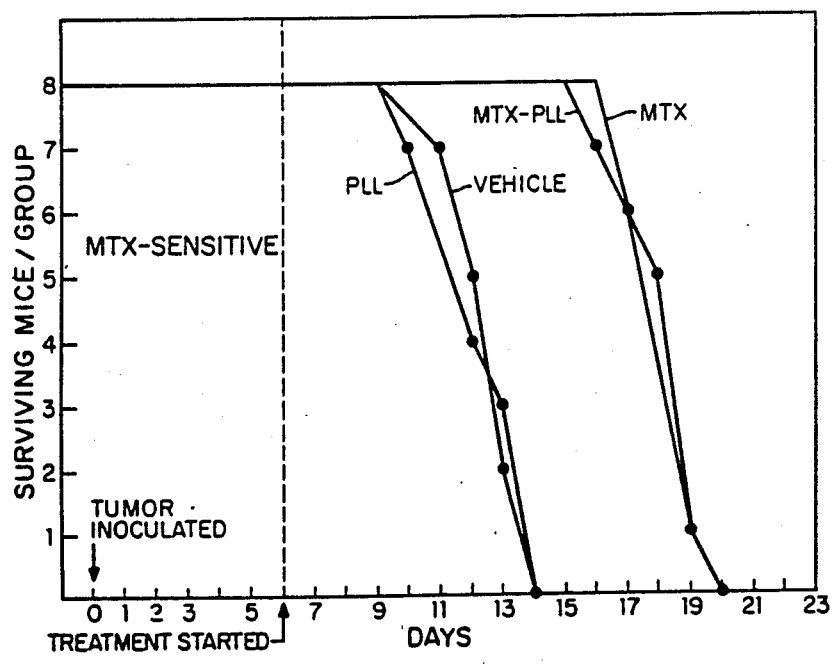
FIGS. 6 and 7 are plots of data illustrating the effect of MTX and MTX-PLL conjugate on the survival of mice bearing an MTX-resistant and an MTX-sensitive lymphosarcoma, respectively.

A comparable experiment was carried out with the MTX-sensitive variant of P 1798 described in the previous Example. The data of this experiment are shown in FIG. 7. As can be seen in this Figure, the two control groups showed an identical pattern of survival, with the first death occurring at days 10 and 11 and the last death occurring at day 14. The two groups receiving either free or conjugated MTX stayed alive in the average 6 days longer than the controls. The first deaths occurred on day 16 and 17 in Groups 4 and 3 respectively, and the longest survival was 20 days in both groups. These data show that free and conjugated MTX have comparable effects when used in the treatment of an MTX-sensitive tumor. When measured from the initiation of treatment, the longest survival was 8 days in the control groups and 14 days in the experimental groups. When the two survival experiments are compared, it appears that the conjugated MTX has a comparable effect in animals bearing either the resistant or the sensitive form of P 1798 lymphosarcoma.

EXAMPLE 25

UPTAKE OF $^3$H-MTX AND $^3$H-MTX-PLL CONJUGATE BY P1798 S/B LYMPHOSARCOMA, IN VIVO

These experiments were carried out with BALB/c mice bearing either a MTX-resistant, steroid-sensitive tumor (P1798 S/B) or a steroid-resistant, presumably MTX-sensitive variant of P1798 S/B. Mice were inoculated subcutaneously with $1\times10^7$ tumor cells and used 12 days after inoculation at a time when the tumor weight was about 5 g. The tumor bearing animals received, in the tail vein, one injection of 0.2 ml $^3$H-MTX or $^3$H-MTX-PLL containing a total of 3.2 and $2.0\times10^6$ CPM, respectively. The $^3$H-MTX-PLL conjugate contained a PLL of 3,100 molecular weight. The amount of MTX injected as free MTX or MTX-PLL were 3.6 mg/kg and 3.2 mg/kg respectively. The mice were sacrificed 24 hours after injection, their tumors were excised and a tissue slice including the center of the tumor was minced and teased through a stainless steel grid to yield a cell suspension. Triplicate aliquots containing $5\times10^6$ cells were processed for radioactive measurements in a liquid scintillation counter, and the average counts were corrected for the difference in total radioactivity injected as free or conjugated drug. The results of two typical experiments were:

| Tumor Type | Exp. No. | CPM Per $5\times10^6$ Cells | | B/A |
|---|---|---|---|---|
| | | $^3$H-MTX (A) | $^3$H-MTX-PLL (B) | |
| MTX-resistant | I | 63 | 6169 | 98 |
| | II | 94 | 6032 | 64.2 |
| MTX-sensitive | I | 2099 | 5921 | 2.8 |
| | II | 2240 | 4480 | 2.0 |

These data demonstrate that intravenously injected $^3$H-MTX-PLL conjugate is readily taken up by both drug-resistant and drug-sensitive tumors in situ and that the uptake of conjugated drug far exceeds the uptake of free drug in both tumors. The average increase in uptake due to conjugation was 81-fold in the case of the drug-resistant tumor and 2.4-fold in the case of the drug-sensitive counterpart. The data show furthermore that, while the conjugated drug is taken up in comparable amounts by the resistant and sensitive tumor, the free drug is taken up to a much lesser extent by the resistant tumor. This difference, which is of the order of 30-fold, strongly suggests that drug resistance of P1798 S/B is due to a deficient drug transport. These data are consistent with those of experiments measuring the cellular transport of the drug in cell suspensions derived from the P1798 S/B tumors. (See Example 26).

EXAMPLE 26

UPTAKE OF $^3$H-MTX AND $^3$H-MTX-PLL By CELL SUSPENSIONS OF P1798 S/B LYMPHOSARCOMA, IN VITRO

A MTX-resistant tumor (P1798 S/B lymphosarcoma) and a MTX-sensitive variant thereof were grown as subcutaneous tumors in BALB/c mice as described in Example 23. Tumors of an average weight of 5 g were excised, minced in RPMI 1640 tissue culture medium, and teased to yield cell suspensions. The disassociated cells were spun down to a loose pellet and resuspended in fresh medium to a cell concentration of $5\times10^6$ cells per 3.0 ml of medium. Comparable suspensions prepared from both tumors received either $4\times10^5$ CPM of $^3$H-MTX or $2.5\times10^5$ CPM of $^3$H-MTX-PLL conjugate. The $^3$H-MTX-PLL preparation was the same as that used in Example 25 (PLL MW 3,100). The molar concentrations of MTX in the incubation medium of the suspensions exposed to MTX and MTX-PLL were $8.8\times10^{-6}$M and $7.3\times10^{-6}$M respectively. The suspensions were incubated for 60 minutes at 37° C. in a $CO_2$-atmosphere, spun down and washed twice with label-free medium. Triplicate aliquots of $1\times10^5$ cells were processed for radioactivity measurements in a liquid scintillation counter, and the average counts were corrected for the difference in the total activity added as free or conjugated drug. The results of two such experiments were:

| Tumor Type | Exp. No. | CPM per $1\times10^5$ Cells | | B/A |
|---|---|---|---|---|
| | | $^3$H-MTX (A) | $^3$H-MTX-PLL (B) | |
| MTX-resistant | I | 277 | 10,050 | 36 |
| | II | 178 | 14,024 | 79 |
| MTX-sensitive | I | 2,094 | 10,549 | 5.0 |
| | II | 3,154 | 13,344 | 4.2 |

These results show that, when exposed to MTX concentrations of approximately $8\times10^{-6}$M, cells derived from the MTX-resistant tumor take up about 10-times less free drug than those derived from the corresponding drug sensitive tumor, while both cell types take up nearly identical amounts of conjugated drug. The data also show that the conjugated drug is taken up much more readily than the free drug by either cell type and that conjugation increases the cellular uptake of MTX by an average factor of 57-fold and 4.6-fold in the case of the drug-resistant and drug-sensitive tumor cells respectively. These results are consistent with the data of Example 25. A comparison of the data of Example 25 and 26 shows a difference in the relative uptake of free MTX by the cells derived from the MTX-sensitive and MTX-resistant tumor. This can be accounted for by the differences in concentration of MTX to which tumor cells were exposed in the in vivo and in vitro experiments. The average ratios of MTX-PLL/MTX taken up by cells of the resistant tumor are of the same order of magnitude (81 and 57) and are indeed very large in both examples. The data of these two examples are also consistent with the previous results obtained with two MTX-resistant and -sensitive lines of Chinese Hamster Ovary cells (see Example 14). They establish that the MTX resistance of the P1798 S/B tumor is indeed due to a deficiency in the membrane transport of MTX.

EXAMPLE 27

UPTAKE OF $^3$H-MTX AND $^3$H-MTX-PLL BY A HUMAN LYMPHOBLASTOID TUMOR LINE

A human lymphoblastoid tumor cell line proficient in MTX transport and a mutant line thereof, deficient in MTX transport and hence drug resistant, were provided by Dr. John S. Erikson, from the Medical College of Pennsylvania. The cells were grown in RPM1 1640 medium containing 10% fetal calf serum.

Uptake experiments were carried out using a microtest plate (Costar, 0.5 ml well volume). The wells contained $1\times10^6$ cells in 0.2 ml complete RPM1 1640 medium. Either free or conjugated $^3$H-MTX were added to a final MTX concentration of $1.1\times10^{-4}$M and $1\times10^{-4}$M, respectively. The number of counts/well were $4\times10^5$ CPM and $2.5\times10^5$ CPM for $^3$H-MTX and $^3$H-MTX-PLL, respectively. The $^3$H-MTX-PLL preparation was the same as that used in Examples 25 and 26. Measurements were carried out in triplicate wells. The plates were incubated for 60 min. at 37° C. in a 5% $CO_2$ atmosphere. At the end of incubation, each well was harvested unto filter disks using a Sketron AS harvester. The discs were dried, placed in 2 ml Liquiflor and counted in a liquid scintillation counter. The cell-bound $^3$H-MTX and $^3$H-MTX-PLL radioactivity of the triplicates was averaged and corrected for the difference in total radioactivity added as free or conjugated drug. The results were:

| Tumor Type | CPM per 1 × 10⁶ Cells | | |
|---|---|---|---|
| | ³H-MTX (A) | ³H-MTX-PLL (B) | B/A |
| MTX-resistant (mutant) | 1,022 | 63,392 | 62 |
| MTX-sensitive (wild type) | 22,610 | 73,400 | 3.2 |

These results show that the MTX-resistance of the human cell mutant is indeed due to a dificient MTX-transport and that the two human lymphoblastoid tumors lines used in this example behave essentially like the two murine lymphosarcoma P1798 S/B used in Examples 25 and 26, and the two CHO-lines described in Example 14.

EXAMPLE 28

INHIBITORY EFFECT OF MTX AND MTX-PLL ON DNA SYNTHESIS OF A HUMAN LYMPHOBLASTOID TUMOR LINE

These experiments used the same two tumor cell lines as described in Example 27. In these two-phase experiments, the cells were first exposed to different concentrations of MTX and MTX-PLL and, after washing, were reincubated in the presence of $^3$H-thymidine. $^3$H-thymidine incorporation was used as an index of DNA synthesis and cell proliferation. Exposure to MTX occurred in multiwell plates. Cells suspended in a complete RPMI 1640 medium at a density of $2.5 \times 10^6$ ml (2 ml per well) were exposed to MTX concentrations of $1.10^{-5}$, $1 \times 10^{-7}$ and $1 \times 10^{-9}$M given either as free or conjugated drug. The MTX-preparation was the same as that used in Examples 23 and 24 and had a PLL of 2,700 molecular weight. The multiwell plates were incubated for 24 hours at 37° C. in a 5% $CO_2$ atmosphere after which the cells were washed twice with 2.0 ml of fresh medium. Triplicate aliquots (75 μL per well) of the washed suspensions were then reincubated in microwells of a Costar microplate, diluted to 0.2 ml with culture medium and 50 μCi of $^3$H-thymidine (25 μL) was added to each well. After an 18 hour incubation at 37° C., the cells were harvested onto filter discs, using a Sketron AS cell harvester. The discs were then dried, placed in scintillation solution and counted in a liquid scintillation counter. The results of a typical experiment, giving the averaged DNA-associated counts of three wells as CMP/well or as percent of control cells, are presented in Table II below.

human cells resistant to MTX are not, or only minimally, influenced by free MTX, they are strongly inhibited by MTX-PLL. Since this inhibitory effect is comparable in magnitude to that caused by MTX in MTX-sensitive cells, it can be concluded that the conjugated drug is capable of totally overcoming drug resistance in a human tumor cell line. It is apparent also that sensitive cells respond in similar fashion to both free and conjugated drug.

The data presented in this example indicate that the growth inhibitory effects recorded on Chinese hamster ovary cells (Examples 15, 17 and 20) and on the murine lymphosarcoma P1978 (Examples 23 and 24) are relevant to the treatment of human tumors.

EXAMPLE 29

COVALENT BONDING (CONJUGATION) OF THE NUCLEOTIDE ANALOG 6-MERCAPTOPURINE RIBOSYLPHOSPHATE (6-MPRP) TO PLL

The nucleotide corresponding to 6-mercaptopurine (6-MP), namely 6-mercaptopurine ribosylphosphate (6-MPRP), was conjugated to PLL, MW 70,000, using the carbodiimide reagent, as described in Example 13 above. The reaction time was reduced to 1 hour at 25° C. Column chromatography of the reaction product on Sephadex G-50 gave a sharp separation of conjugated and free 6-MPRP. The 2 forms of 6-MPRP had comparable UV absorption spectra, indicating that conjugation had not caused any modification of the mercaptopurine moiety.

EXAMPLE 30

CYTOCIDAL EFFECTS OF 6-MPRP AND 6-MPRP-PLL CONJUGATE ON L-929 FIBROBLAST CELLS

Cytocidal effects of 6-MRPP-PLL conjugate and of unconjugated 6-MPRP plus free PLL were compared using monolayer cultures of L-929 fibroblasts. Sparse monolayers in phase of exponential growth were exposed to $1 \times 10^{-5}$M free or conjugated 6-MPRP for 1 h, 24 h after inoculation. After exposure to the free or conjugated drug, the monolayers were kept growing for 2 days in standard growth medium, at which time no cytocidal effect could be detected. When the cells were subcultured and incubated for 7 additional days, the cells exposed to 6-MPRP-PLL failed to show any growth while cells exposed to a combination of free 6-MPRP and free PLL grew at a rate undistinguichable from that of controls. A preparation of 6-MPRP-PLL

TABLE 2

| Cell type | MTX[1] Concentration in Medium (M) | No Drug (CPM) | ³H—Thymidine incorporation into DNA of cells exposed to | | | | |
|---|---|---|---|---|---|---|---|
| | | | MTX | | MTX-PLL | | |
| | | | (CPM) | (%)A | (CPM) | (%)B | A–B[2] |
| MTX-Resistant | 0 | 59,989 | — | — | — | — | — |
| | 10⁻⁹ | — | 59,862 | (101) | 61,099 | (104) | 0 |
| | 10⁻⁷ | — | 61,059 | (103) | 49,431 | (84) | 19 |
| | 10⁻⁵ | — | 49,341 | (84) | 17,681 | (30) | 54 |
| MTX-Sensitive | 0 | 64,568 | — | — | — | — | — |
| | 10⁻⁹ | — | 62,5–7 | (97) | 68,234 | (106) | 0 |
| | 10⁻⁷ | — | 51,451 | (80) | 53,671 | (91) | 0 |
| | 10⁻⁵ | — | 15,679 | (24) | 24,439 | (38) | 0 |

[1]Either in free or conjugated form
[2]Increased inhibition obtained with drug in conjugated form (% of control)

These data demonstrate that human tumor cells can be inhibited by MTX-PLL. They show that while that had been briefly trypsinized caused a 50% inhibition of cell growth. Under other experimental conditions, i.e., when 6-MPRP and 6-MPRP-PLL were present for the duration of the experiment at a concentration of $2\times10^{-6}$M, both compounds had inhibiting effects.

Figure 8:
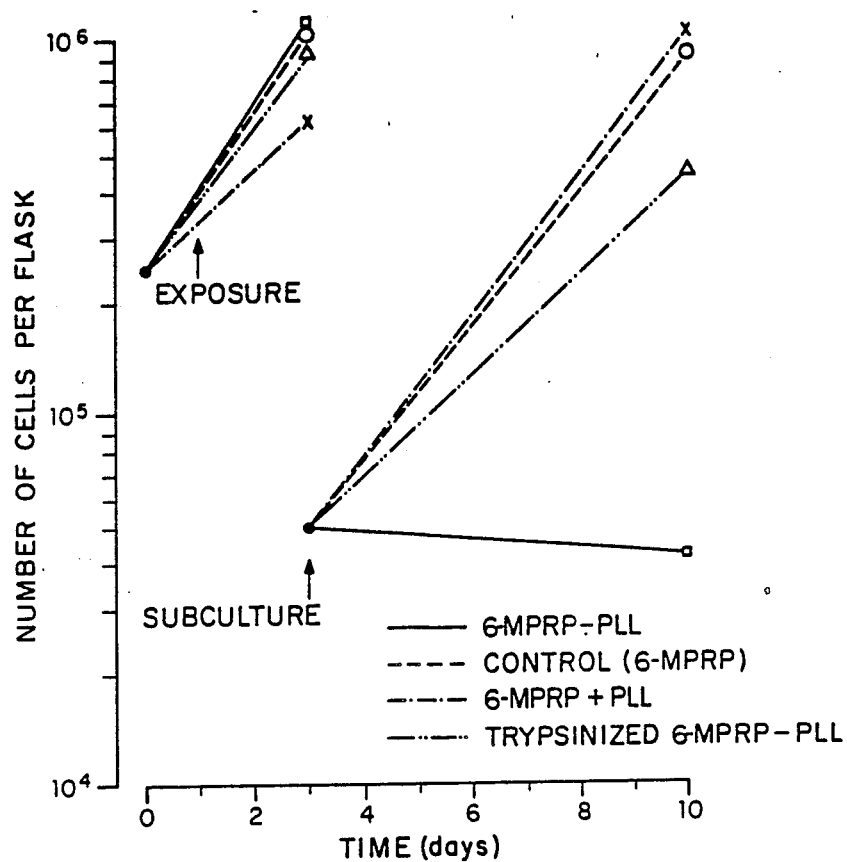
FIG. 8 is a plot illustrating the growth of L-929 fibroblasts following their brief exposure to free 6-mercaptophosphoribosylpurine (6-MPRP), a mixture of free 6-MPRP and free Poly-L-lysine (PLL), conjugated 6-MPRP-PLL, and trypsinized 6-MPRP-PLL conjugate.

The data obtained are plotted in FIG. 8 and demonstrate: (1) that the 6-MPRP-PLL conjugate possesses biological activity; (2) that the conjugate can kill cells after a very short time of exposure in experimental conditions under which the free nucleotide is ineffective; and (3) that a nucleotide analog can be made to penetrate cells by employing PLL-conjugation.

EXAMPLE 31

CELLULAR UPTAKE OF $^{125}$I-LABELED HOMOPOLYMERS OF L-LYSINES

Poly-L-lysines of three different average molecular weights, i.e., 38,000, 115,000 and 230,000, were radioiodinated using the Bolton-Hunter Reagent. See Bolton, A. E. and Hunter, W. M., *Biochem J.*, 133, pp 529–38 (1973). Unreacted $^{125}$I-Bolton-Hunter Reagent was eliminated by chromatography on Biogel P-60 followed by extensive dialysis.

Monolayers of Sarcoma S-180, an established tumor cell line, were grown to confluence in Eagle's medium and were used to measure cellular uptake of $^{125}$I-PLL. The poly-L-lysine concentration in the medium was 3 $\mu$g/ml throughout. The experiment was carried out following the procedure described in Example 3 for the measurement of $^{125}$I-HSA except that measurements were made after one and sixty mins. of incubation at 37° C. The results, corrected for the relative purity and specific radioactivity of the three poly-L-lysine polymers, were as follows:

| MW of PLL | No. of Measurements | Concentration (nM) | Uptake (ng/mg cell protein) | | 60-min (Corrected for Concentration of 79 nM) |
|---|---|---|---|---|---|
| | | | 1-min | 60-min | |
| 38,000 | 11 | 79 | 18.8 | 349.4 | 349 |
| 115,000 | 9 | 24 | 112.3 | 513.3 | 1717 |
| 250,000 | 8 | 13 | 153.7 | 695.4 | 4209 |

As can be seen from these data, labeled poly-L-lysines are readily taken up by cells in a time-dependent fashion. When the three species of polymers are used in the same weight per volume concentration (3 $\mu$g/ml), their absolute uptake increases with their molecular size.

Figure 9:
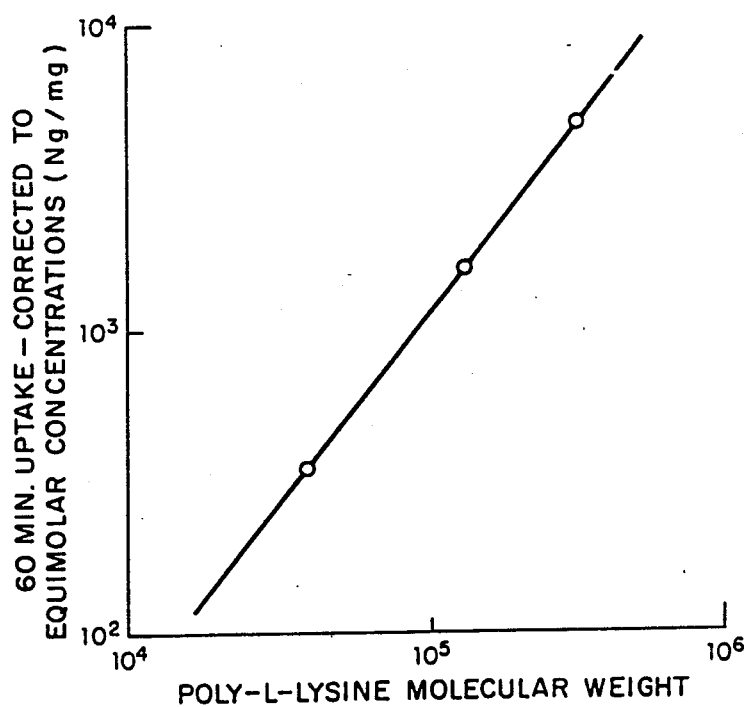
FIG. 9 is a plot illustrating the cellular uptake of labeled poly-L-lysine of varying molecular weight corrected to equimolar concentrations.

Considering that under these experimental conditions the molar concentration of the 3 polymers, was 79, 24 and 13 nM, respectively, and assuming that the uptake is linear with concentration in that range, the values above can be corrected for a uniform concentration of 79 nM. These corrected values (last column) show a log-linear relationship to the molecular weight, as shown in FIG. 9. These results show that the cellular uptake of homopolymers of L-lysine increases linearly with their size.

EXAMPLE 32

INTRACELLULAR BREAKDOWN OF INGESTED $^{125}$I-PLL BY SARCOMA S-180 CELL MONOLAYERS

Figure 10:
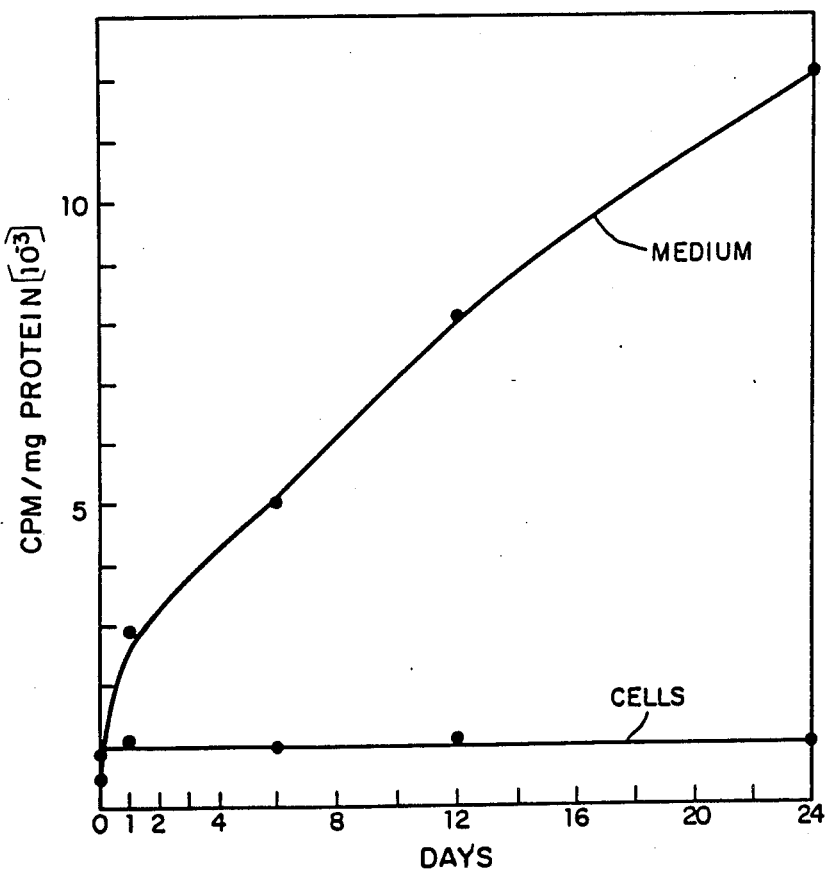
FIG. 10 is a plot of data illustrating the level of intracellular breakdown products of $^{125}$I-PLL ingested by Sarcoma S-180 cell monolayers which are present in the cells and in the cell medium.

Confluent monolayers of Sarcoma S-180 were grown as described in Example 31. They were incubated for 60 minutes in serum free medium containing 0.2 $\mu$g/ml of $^{125}$I-PLL, of 115,000 molecular weight and high specific radioactivity. At the end of this incubation period, the labeled medium was removed and the monolayers were thoroughly washed with buffered salt solution (BSS). The monolayers were then reincubated in non-radioactive conditioned growth medium for various periods of time up to 24 hours. At each time, measurements were made of the acid soluble radioactivity both in the medium and in the cells. The acid soluble radioactivity of the medium was measured in the supernatant of medium treated at a final concentration of 20% trichloroacetic acid (TCA). The acid soluble radioactivity of the cells was measured by trypsinization of the monolayers, thorough washing of the detached cells, and precipitation of their acid insoluble cellular components with a final concentration of 20% TCA. FIG. 10 represents the results of a typical experiment and shows the generation of TCA soluble labeled breakdown product of $^{125}$I-PLL as a function of time.

The upper curve, corresponding to the acid soluble radioactivity of the culture medium, shows that labeled breakdown product of $^{125}$I-PLL are released into the medium over the total period of reincubation and that this release increases linearly between 1 and 12 hours. By contrast, the cell-associated acid soluble radioactivity remained essentially constant over a period of 24 hours.

These data suggest that PLL transported into cells during a 1 hour period of incubation is broken down inside the cell into small acid soluble products, of which a small and constant amount is retained by the cell, while an increasing amount is excreted and accumulates in the growth medium. It should be noted that the PLL was labeled with the Bolten-Hunter reagent and that the labeled lysyl or oligolysyl adducts, unlike the unlabeled lysine arising from intracellular digestion, cannot be reutilized by the cell for protein biosynthesis.

EXAMPLE 33

CELLULAR UPTAKE OF $^{125}$I-PLL AND $^{125}$I-PDL BY A BHK CELL LINE HAVING A TEMPERATURE SENSITIVE MALIGNANT PHENOTYPE

This experiment was done with a baby hamster kidney cell line (BHK) transformed by exposure to dimethylnitrosamine (DMN), growing with a non-malignant phenotype at 32° C. and a malignant phenotype at 38.5° C. This temperature-sensitive mutant line, called BHK (DMN$^{ts}$) was described by G. DeMayorca et al. *Proc. Natl. Acad. Sci U.S.A.*, 70, 46–49 (1973). The cells were grown as monolayers in Dulbecco's high glucose medium. The transition from normal to transformed phenotype requires 3 to 4 population doublings or approximately 56 hours of growth at 38.5° C. The reversion to the normal, non-malignant phenotype likewise require 3 to 4 population doublings or approximately 112 hours of growth at 32° C. PPL and PDL of average molecular weights of 125,000 and 130,000, respectively, were radioiodinated as described in Example 31. At time 0, the growth media of the confluent monolayers were replaced by serum free medium prewarmed to 37° C. and containing 3 $\mu$g/ml radioiodinated polymer. The monolayers were then incubated for 60 min. at 37° C. At the end of incubation, the cells were washed, detached, washed further and processed for measurement of $^{125}$I radioactivity as described in Example 31. The results were as follows:

| Phenotype | Cellular Uptake in 60 min. (ng/mg cell protein) | |
|---|---|---|
| | PLL | PDL |
| Normal | 525 | 685 |
| Transformed | 750 | 680 |
| Transformed/Normal | 1.43 | 1 |

These data show that PLL is taken up more effectively by cells of the transformed phenotype than by cells of normal phenotype. A comparable difference, however, is not apparent in the uptake of PDL. This finding suggests that malignant growth behavior may be associated with greater cellular uptake of PLL, and hence of PLL conjugate. This example of preferential uptake is of interest because it would be highly desirable for the purpose of selective toxicity in cancer chemotherapy to achieve greater transport of cancer drugs into malignant cells.

EXAMPLE 34

INTRACELLULAR BREAKDOWN OF INGESTED $^{125}$I-PLL AND $^{125}$I-PDL BY BHK(DMN) Ts CELLS AT PERMISSIVE AND NON-PERMISSIVE TEMPERATURES

This experiment employed the cells described in the preceding example. The cells were grown, and exposed to radiolabeled PLL or PDL as described in Example 33 except that the labeled polymer concentration was approximately 0.3 μg/ml. After the 60 min. incubation at 37° C., the labeled medium was removed, and monolayers were thoroughly washed with buffered saline solution. An additional wash with saline containing 25 mg/ml dextran sulfate was carried out to remove surface-bound $^{125}$I-polymers. The monolayers of cells with either phenotype were then reincubated for 24 hours at 32° C. in the presence of unlabeled conditioned medium, after which the radioactivity of the medium and of the cells were measured separately. A second set of monolayers of either phenotype was reincubated for 24 hours at 38.5° C. and processed in similar fashion. The total radioactivity measured in the medium and in the cells was expressed as ng $^{125}$I-PLL per mg cell protein. The results were:

| Temp. of Reincubation | Phenotypic State | Radioactivity (ng $^{125}$I-PLL) per mg Cell Protein | | | |
|---|---|---|---|---|---|
| | | In Medium(a) | | In Cells | |
| | | PLL | PDL | PLL | PDL |
| 32° | Normal | 13.6 | 3.29 | 12.4 | 21.5 |
| | Transformed | 20.4 | 3.63 | 11.3 | 30.1 |
| 38.5° | Normal | 20.6 | 4.87 | 11.8 | 20.1 |
| | Transformed | 26.9 | 6.06 | 9.7 | 35.7 |

(a)A large fraction of the medium (35 to 60%) was acid soluble.

These data show that the radioactivity introduced into the cells as $^{125}$I-PDL tends to remain in the cells rather than to appear in the culture medium while a large fraction of PLL radioactivity disappears from the cells and is excreted into the medium. That the higher cell-bound radioactivity of cells exposed to $^{125}$I-PDL is not due to a greater cellular uptake can be inferred from the data of Example 33, which show that cellular uptake of the two isomers is of comparable magnitude. These data, together with those of Example 32, provide independent evidence that ingested PLL is readily hydrolyzed inside the cells to small molecular diffusible breakdown products, while ingested PDL is not. These observations are consistent with those of Example 16, 17, 18 and 19 comparing the properties of MTX-PLL and MTX-PDL, and of Example 36 comparing the stability of HSA-PLL and HSA-PDL complexes.

More importantly, this Example shows that cells of the transformed phenotype tend to excrete a greater fraction of ingested PLL radioactivity into the medium than cells of a normal phenotype, suggesting a more efficient intracellular breakdown of PLL by cell of malignant phenotype. This difference is seen regardless of the temperature at which the experiment is carried out. This finding is of importance in view of the data we obtained with animal and human tumor cells (see Examples 23, 24 and 28). Indeed, for the purpose of selectivity in cancer chemotherapy with drug-poly(L-lysine) conjugate, it would be advantageous if a more effective breakdown of the PLL carrier occurred in malignant that in non-malignant cells.

EXAMPLE 35

CELLULAR UPTAKE OF TRYPAN BLUE-PLL COMPLEXES COMPARED TO THAT OF FREE TRYPAN BLUE

Trypan Blue, an anionic dye commonly used in histology, has the property of being excluded by intact healthy normal cells and is often used to test the integrity of living cultured cells. We observed that when PLL of 70,000 NW is added to an aqueous solution of Trypan Blue, it forms non-covalent soluble complexes which possess totally different staining properties than free Trypan Blue.

Sparse monolayers of L 929 mouse fibroblasts grown on coverslips in Eagles medium were exposed overnight to growth medium containing 100 μg/ml Trypan Blue and 30 μg/ml PLL. The coverslips were thoroughly washed, fixed with 2.5% glutaraldehyde, dehydrated and mounted as permanent cytologic slides. Microscopic observation of these slides and photomicrographs thereof showed marked dye uptake by otherwise healthy looking cells. The cellular distribution of the dye was strikingly similar to that of horseradish peroxidase reaction products following exposure of cells to HRP-PLL, and described in Example 7A. The intensity of staining was time and concentration dependent. Since the dye is totally excluded by healthy cells in the absence of PLL, and since PLL is readily taken up by cells (see Examples 31, 32, 33 and 34), it is concluded that in this instance, the dye is transported into cells as a PLL-complex in which PLL acts as a carrier molecule. Thus, a small anionic molecule can, under circumstances, form non-covalent complexes with PLL which are so strong as to assume the properties of covalent PLL-conjugates. This observation opens the possibility of using dye-PLL complexes for rapid screening of membrane transport or tissue distribution of PLL.

EXAMPLE 36

COMPLEXES OF POLY-L-LYSINE (PLL), POLY-D-LYSINE (PDL), POLY-L-ORNITHINE (PLO), AND POLY-L-HOMOARGININE (PLHA) WITH HUMAN SERUM ALBUMIN (HSA): THEIR SUSCEPTIBILITY TO TRYPSIN AND HEPARIN

It was shown that free PLL and PDL when added to an incubation medium containing $^{125}$I-HSA had strikingly different effects on the cellular uptake of $^{125}$I-HSA. This difference prompted a study of their in vitro interaction with $^{125}$I-HSA. Both polymers were found to form, in the presence of HSA, aggregates that could be quantitated by simple turbidity measurements in a spectrophotometer. PLL of low molecular weight, which—as previously reported—are unable to enhance the uptake of HSA, did not cause measurable aggregation of HSA in vitro. These two results suggested that in vitro aggregation might bear some relationship to the enhancement of HSA-uptake.

Since in the standard procedure used to measure the cellular uptake of albumin, cell monolayers are detached from the culture flasks by brief trypsinization, the effect of trypsin on the poly(lysine)-HSA complex observed in vitro was investigated. HSA (0.5 mg/ml) and the poly(amino acids) (10 µg/ml) were mixed in a 3 ml cuvette in balanced salt solution (BSS) without phenol red. The change of absorption at 420 nm due to the turbidity was used as the measurement of the aggregate formation and dissociation. Trypsin solution (30 µl of 0.25%) was added at 15 minutes to both PLL and PDL samples. Heparin solution (30 µl of 5 mg/ml) was added at 30 minutes to the PDL sample.

Figure 11:
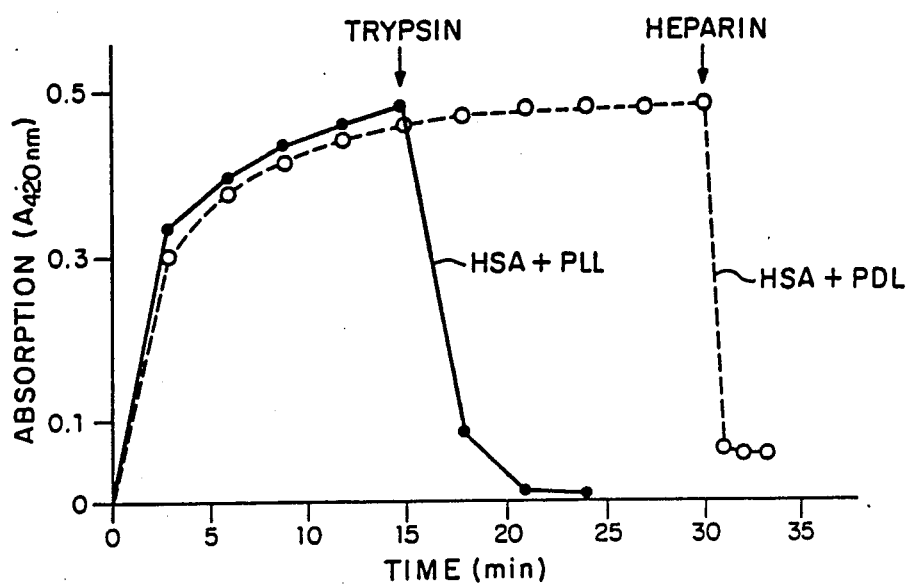
FIG. 11 is a plot illustrating the in vitro effect of trypsin and heparin addition upon aggregates of human serum albumin (HSA) and poly-L-lysine (PLL) and aggregates of HSA and poly-D-lysine (PDL); and, FIG. 12 is a plot illustrating the in vitro effect of trypsin upon aggregates of HSA and each of poly-L-lysine (PLL), poly-L-ornithine (PLO) and poly-L-homoarginine (PLHA).

FIG. 11 shows that the rate of aggregate formation initiated by the mixture of HSA and poly(lysines) can be followed spectrophotometrically and that the rate is identical for both isomers. When the turbidity had reached a plateau, the addition of trypsin completely dissolved the aggregates of HSA-PLL, but had no effect on the aggregates of HSA-PDL. The latter aggregate, however, could be dissociated to a large extent by the addition of 5 mg/ml heparin, a strong polyanion.

Figure 12:
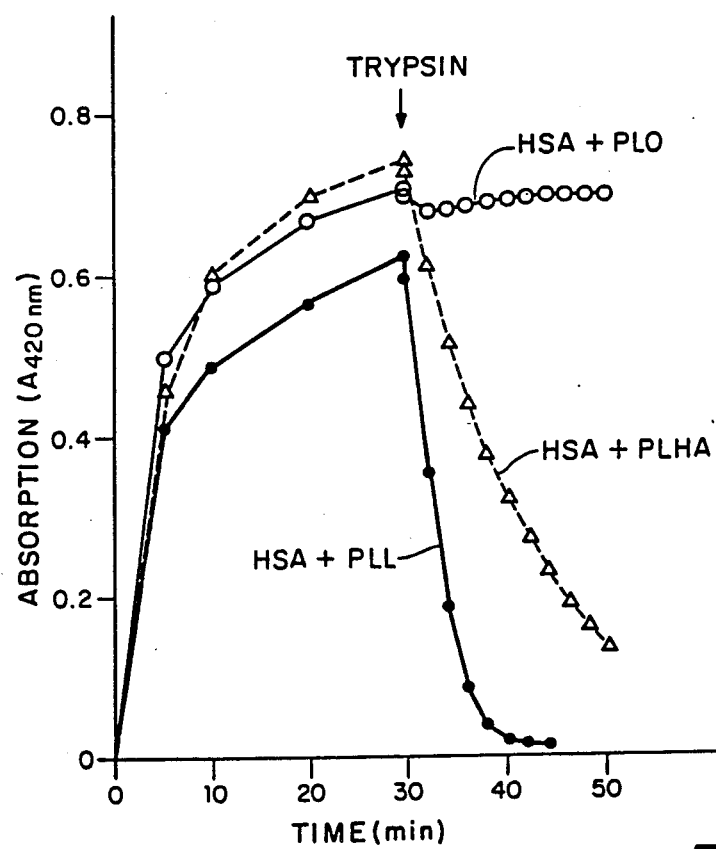

Similar experiments were carried out with PLO and with PLHA except that the PLHA concentration was 30 µg/ml and trypsin was added after 30 minutes. The HSA-PLHA complexes showed intermediate susceptibility to trypsin, as shown in FIG. 12.

Those skilled in the art will recognize many equivalents to the specific embodiments of the invention described herein. For example, it is believed that non-covalent bonding could be employed with this invention if the bond strength approached that of covalent bonds. Such equivalents are considered to be part of this invention and are intended to be encompassed by the scope of the following claims.

What is claimed is:

1. A conjugate comprising a nucleotide analogue which is poorly transported into cells covalently bonded to a cationic polymer, said conjugate having enhanced cellular uptake compared to said nucleotide analogue and wherein said nucleotide analogue is 6-mercaptophosphoribosyl purine, cytosine arabinosylphosphate or adenosine arabinosylphosphate.

* * * * *